US010867718B2

(12) United States Patent
Liu et al.

(10) Patent No.: US 10,867,718 B2
(45) Date of Patent: Dec. 15, 2020

(54) MECHANICALLY INTERLOCKED AIR-STABLE RADICALS

(71) Applicant: Northwestern University, Evanston, IL (US)

(72) Inventors: Zhichang Liu, Evanston, IL (US); Junling Sun, Albany, NY (US); James Fraser Stoddart, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/032,212

(22) Filed: Jul. 11, 2018

(65) Prior Publication Data

US 2019/0016737 A1 Jan. 17, 2019

Related U.S. Application Data

(60) Provisional application No. 62/531,115, filed on Jul. 11, 2017.

(51) Int. Cl.
| | |
|---|---|
| *H01B 1/12* | (2006.01) |
| *C07D 401/14* | (2006.01) |
| *C07D 519/00* | (2006.01) |
| *C07D 471/06* | (2006.01) |
| *C30B 29/54* | (2006.01) |

(52) U.S. Cl.
CPC .......... *H01B 1/122* (2013.01); *C07D 401/14* (2013.01); *C07D 471/06* (2013.01); *C07D 519/00* (2013.01); *C30B 29/54* (2013.01)

(58) Field of Classification Search
CPC .......... H01B 1/12; H01B 1/121; H01B 1/122; C07D 221/18; C07D 401/14; C07D 471/02; C07D 471/06; C07D 487/02; C07D 487/06; C07D 519/00; C30B 29/54; C07B 2200/13
See application file for complete search history.

(56) References Cited

U.S. PATENT DOCUMENTS

| | | | | |
|---|---|---|---|---|
| 6,198,655 B1* | 3/2001 | Heath | | B82Y 10/00 365/151 |
| 8,946,454 B2* | 2/2015 | Yaghi | | B01J 20/226 549/351 |
| 9,120,799 B2 | 9/2015 | Fahrenbach | | |
| 2014/0179017 A1 | 6/2014 | Stoddart | | |
| 2015/0191470 A1* | 7/2015 | Fahrenbach | | C07D 471/22 526/259 |

OTHER PUBLICATIONS

Ashton et al. ("Diazapyrenium-containing catenanes and rotaxanes," New J. Che., 23, 587-602). (Year: 1999).*
Fang et al. ("Syntheses and dynamics of donor-acceptor [2]catenanes in water," J. Am. Chem. Soc., 133, 396-399). (Year: 2011).*
Ashton, Peter R., et al. "Diazapyrenium-containing catenanes and rotaxanes." New Journal of Chemistry 23.6 (1999): 587-602.
Barnes, Jonathan C., et al. "A radically configurable six-state compound." Science 339.6118 (2013): 429-433.
Barnes, Jonathan C., et al. "Solid-state characterization and photoinduced intramolecular electron transfer in a nanoconfined octacationic homo [2] catenane." Journal of the American Chemical Society 136.30 (2014): 10569-10572.
Barnes, Jonathan C., et al. "Synthesis of Ex n Box Cyclophanes." The Journal of organic chemistry 78.23 (2013): 11962-11969.
Chen, Lan, et al. "Quadruple switching of pleated foldamers of tetrathiafulvalene-bipyridinium alternating dynamic aovalent polymers." Angewandte Chemie International Edition 54.13 (2015): 4028-4031.
Cheng, Chuyang, et al. "Energetically demanding transport in a supramolecular assembly." Journal of the American Chemical Society 136.42 (2014): 14702-14705.
Fahrenbach, Albert C., et al. "Solution-phase mechanistic study and solid-state structure of a tris (bipyridinium radical cation) inclusion complex." Journal of the American Chemical Society 134.6 (2012): 3061-3072.
Fang, Lei, et al. "Syntheses and Dynamics of Donor-Acceptor [2] Catenanes in Water." Journal of the American Chemical Society 133.3 (2011): 396-399.
Gomberg, M. "An instance of trivalent carbon: Triphenylmethyl." Journal of the American chemical Society 22.11 (1900): 757-771.
Hicks, Robin G., et al. "Strong supramolecular-based magnetic exchange in p-stacked radicals. structure and magnetism of a hydrogen-bonded verdazyl radical: hydroquinone molecular solid." Journal of the American Chemical Society 123.29 (2001): 7154-7159.
Hünig, S.; "DCNQIs—new electron acceptors for charge-transfer complexes and highly conducting radical anion salts." Advanced Materials 3.5 (1991): 225-236.
International Searching Authority, International Search Report and Written Opinion for application PCT/US2018/041551, dated Sep. 28, 2018.
Jeon, Woo Sung, et al. "A [2] Pseudorotaxane-Based Molecular Machine: Reversible Formation of a Molecular Loop Driven by Electrochemical and Photochemical Stimuli." Angewandte Chemie International Edition 42.34 (2003): 4097-4100.

(Continued)

*Primary Examiner* — Matthew R Diaz
(74) *Attorney, Agent, or Firm* — Quarles & Brady LLP; Tolga Gulmen

(57) ABSTRACT

Provided herein are mechanically interlocked air-stable persistent organic radicals. The radical compositions may access a multiplicity of radical, cationic redox states as well as a fully cationic redox state. A composition comprises a first ring mechanically interlocked with a second ring or a salt thereof, wherein the first ring comprises a 4,4'-bipyridinium subunit or a derivative thereof and a diazapyrenium subunit or a derivative thereof and the second ring comprises a 4,4'-bipyridinium subunit or a derivative thereof. In some embodiments, the second ring further comprises a diazapyrenium subunit or a derivative thereof. Methods of preparing the compositions are also provided.

11 Claims, 16 Drawing Sheets

(56) References Cited

OTHER PUBLICATIONS

Kosower, E. M.; "Stable free radicals. II. The reduction of 1-methyl-4-cyanopyridinium ion to methylviologen cation radical." Journal of the American Chemical Society 86.24 (1964): 5524-5527.

Lilienthal, Ninette D., et al. ""N, N'-dimethyl-2, 7-diazapyrenium: a redox-dependent receptor for aromatic carboxylates."" Journal of Electroanalytical Chemistry 414.2 (1996): 107-114.

Liu, Zhaojun, et al. "Effects of gradual oxidation of aromatic sulphur-heterocycle derivatives on multilevel memory data storage performance." Journal of Materials Chemistry C 3.9 (2015): 2033-2039.

Morita, Yasushi, et al. "Organic tailored batteries materials using stable open-shell molecules with degenerate frontier orbitals." Nature materials 10.12 (2011): 947.

Nishinaga, Tohru, and Koichi Komatsu. "Persistent p radical cations: self-association and its steric control in the condensed phase." Organic & biomolecular chemistry 3.4 (2005): 561-569.

Sun, Junling, et al. "An electrochromic tristable molecular switch." Journal of the American Chemical Society 137.42 (2015): 13484-13487.

Zhu, Zhixue, et al. "Controlling Switching in Bistable [2] Catenanes by Combining Donor-Acceptor and Radical-Radical Interactions." Journal of the American Chemical Society 134.28 (2012): 11709-11720.

* cited by examiner

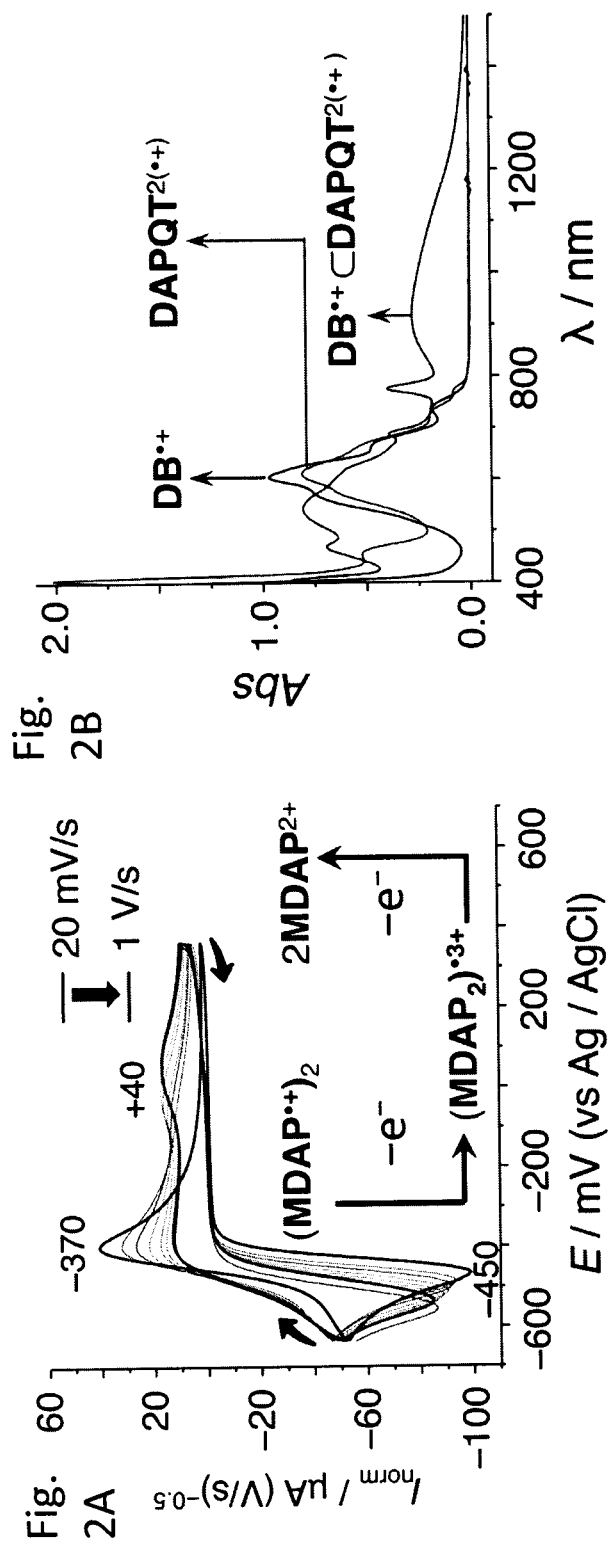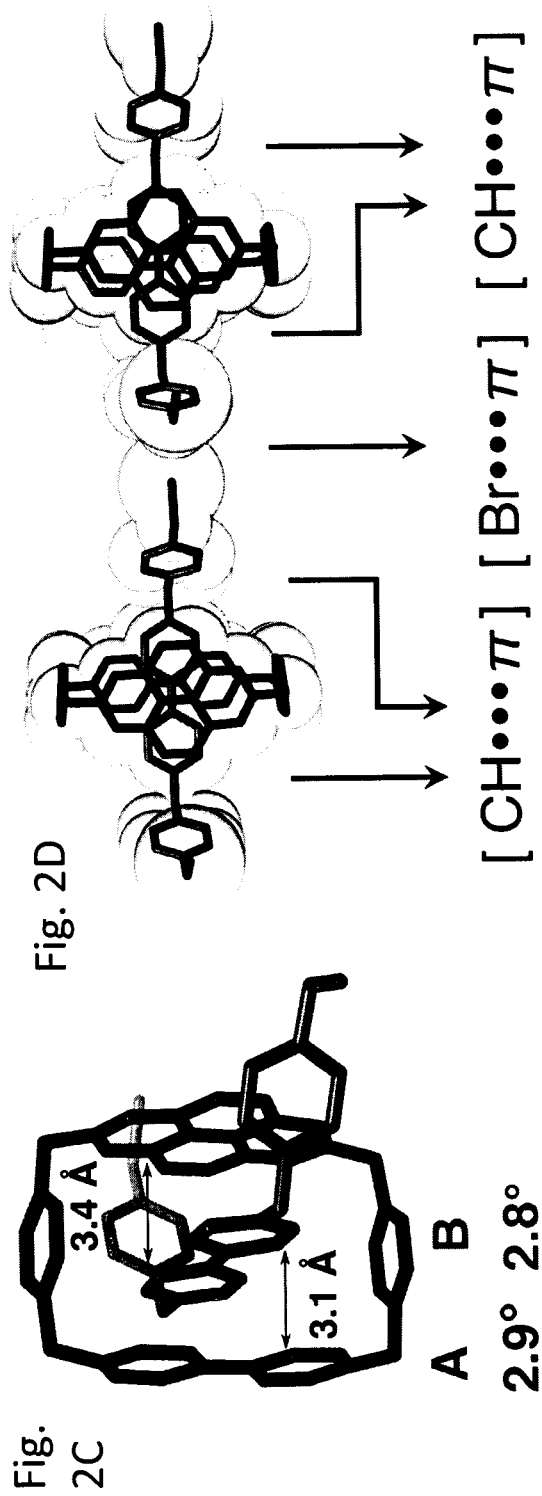
Fig. 2A, Fig. 2B, Fig. 2C, Fig. 2D

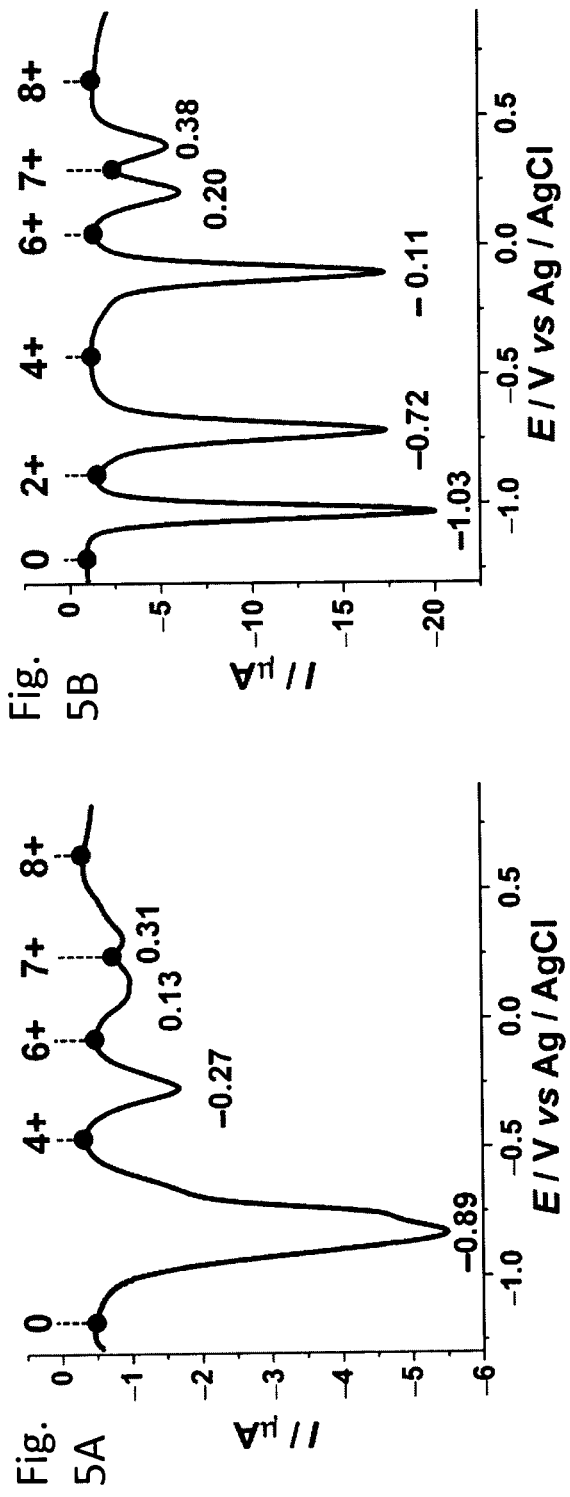
Fig. 5A
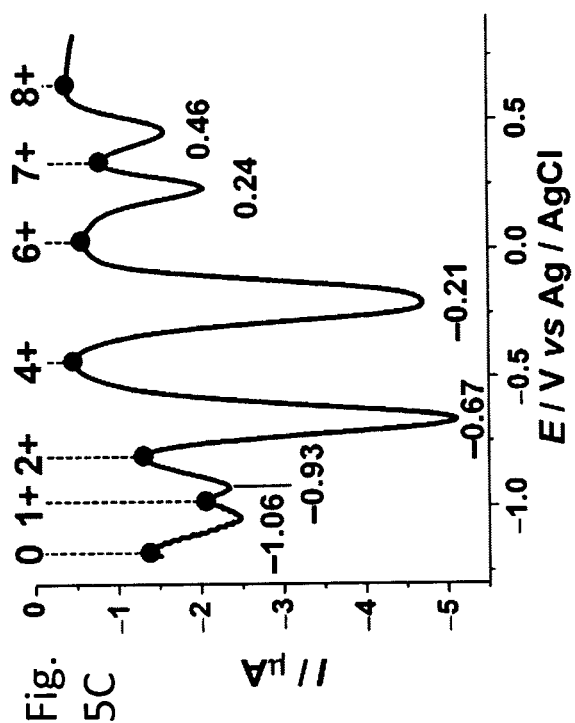
Fig. 5B
Fig. 5C

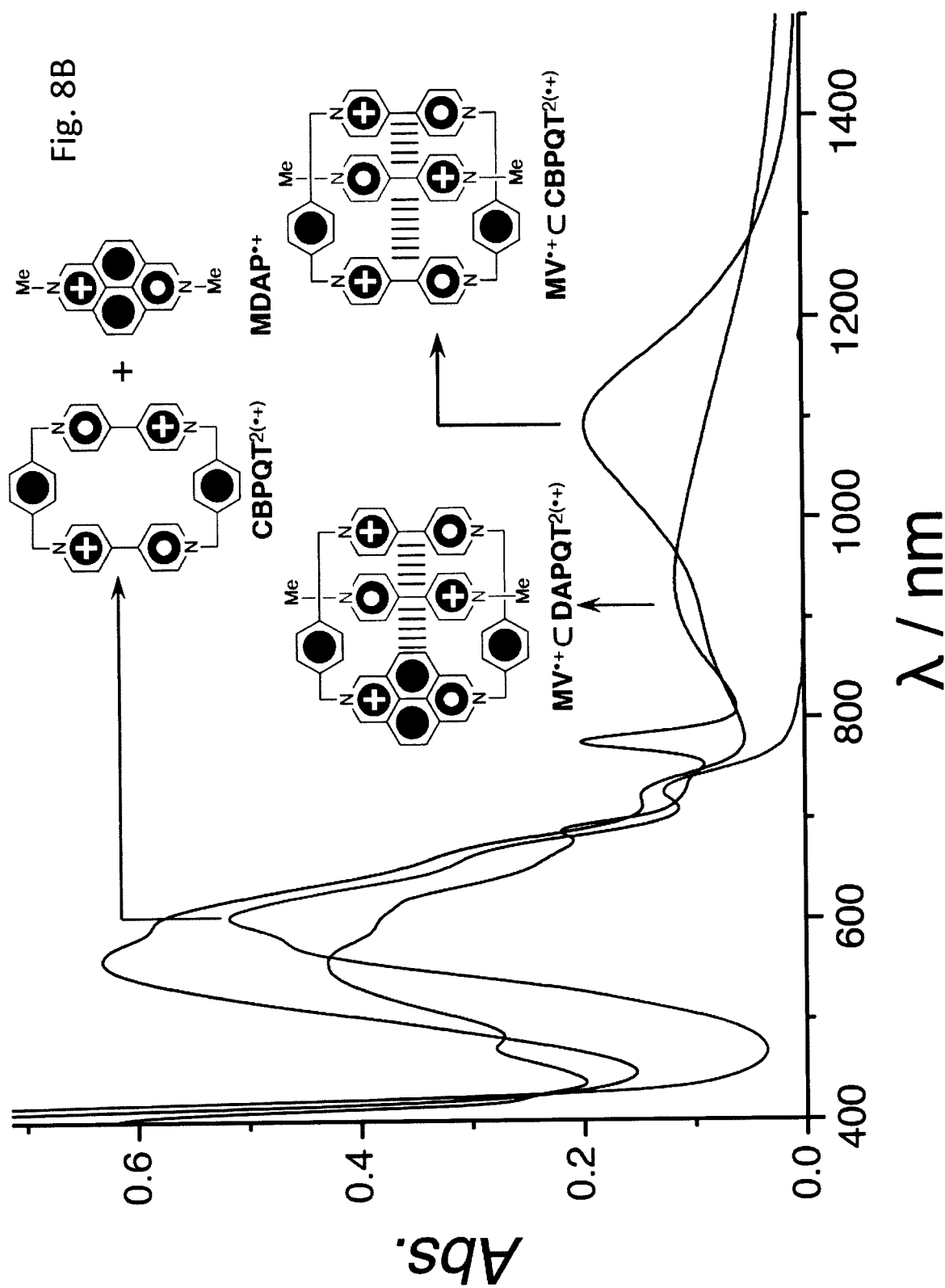

| A | B |
|---|---|
| 2.9° | 2.8° |

MECHANICALLY INTERLOCKED AIR-STABLE RADICALS

CROSS-REFERENCE TO RELATED APPLICATIONS

This application claims benefit of priority to U.S. Provisional Application No. 62/531,115, filed 11 Jul. 2017, the content of which is incorporated herein by reference it its entirety.

FIELD OF INVENTION

The technology generally relates to mechanical bond-protected air-stable persistent organic radicals and methods for making the same. More particularly, the technology relates to compositions comprising a first ring having a 4,4'-bipyridinium subunit or a derivative thereof and a diazapyrenium subunit or a derivative thereof as well as methods for making the same.

BACKGROUND

Ever since the landmark discovery of the triphenylmethyl radical[1] by Moses Gomberg, research on stable organic radicals[2] has attracted attention, not only on account of their exotic electronic properties, but also because of their potential applications as spin-labels[3] and in organic lithium batteries[4] as well as in conductive and magnetic materials.[5] To date, however, most organic radicals experience a fleeting existence and readily undergo dimerization and/or oxidation. The synthesis and isolation of persistent radicals in crystalline forms remains a challenge. In addition, molecular systems with adjustable number of accessible redox states are quite difficult to achieve.

SUMMARY OF THE INVENTION

Provided herein are mechanically interlocked air-stable persistent organic radicals. The radical compositions may access a multiplicity of radical, cationic redox states as well as a fully cationic redox state. The composition comprises a first ring mechanically interlocked with a second ring or a salt thereof, wherein the first ring comprises a 4,4'-bipyridinium subunit or a derivative thereof and a diazapyrenium subunit or a derivative thereof and the second ring comprises a 4,4'-bipyridinium subunit or a derivative thereof. In some embodiments, the second ring further comprises a diazapyrenium subunit or a derivative thereof. In certain embodiments, the composition may comprise a composition of Formula V,

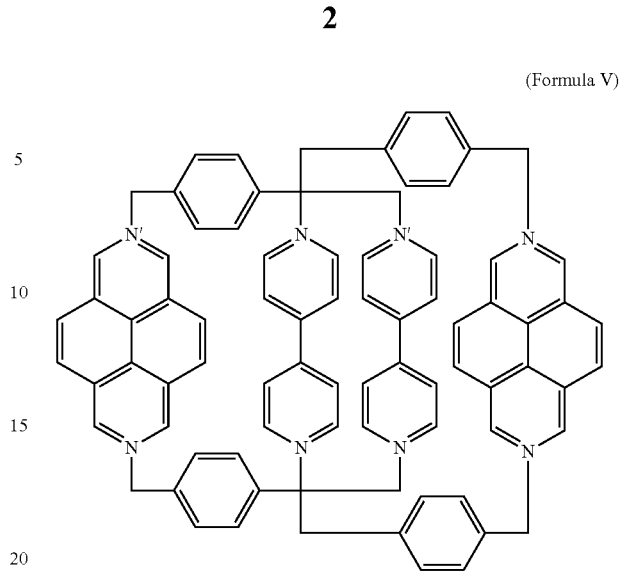
(Formula V)

a derivative thereof, or a salt thereof or a composition of Formula VI,

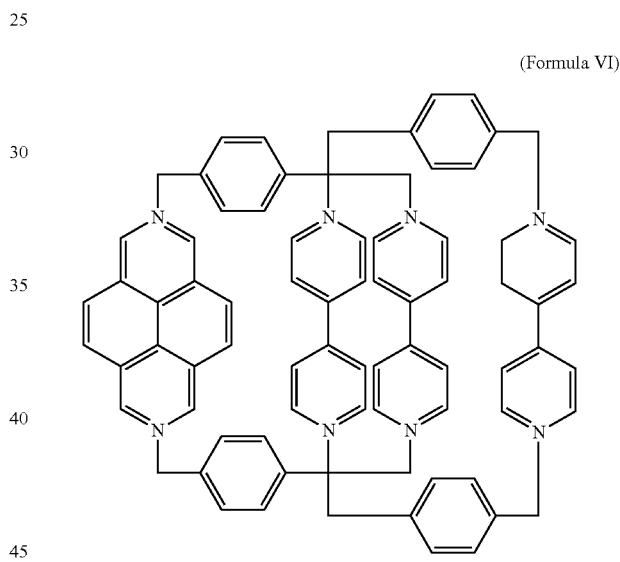
(Formula VI)

a derivative thereof, or a salt thereof.

Another aspect of the invention is crystalline compositions comprising [2]catenanes. The crystalline composition may comprise any of the compositions described herein and having a molecular packing arrangement defined by triclinic space group P$\bar{1}$ (no. 2). In some embodiments, the crystalline composition comprises a crystalline material having lattice parameters of (i) a=13.5±0.1 Å, b=16.5±0.1 Å, c=22.5±0.1 Å, α=86.1±0.1°, β=88.9±0.1°, γ=82.5±0.1° or (ii) a=13.3±0.1 Å, b=27.9±0.1 Å, c=31.5±0.1 Å, α=73.4±0.1°, β=89.8±0.1°, γ=81.0±0.1°.

Another aspect of the technology is a method for preparing a composition. The method comprises providing a radical cationic inclusion complex and reacting the complex with (i) 2,7-diazapyrene (ii) 4,4'-bipyridine, or a derivative of either (i) or (ii), wherein the complex comprises a ring comprising a 4,4'-bipyridinium subunit or a derivative thereof and a diazapyrenium subunit or a derivative thereof. In some embodiments, the ring comprises a compound of Formula III,

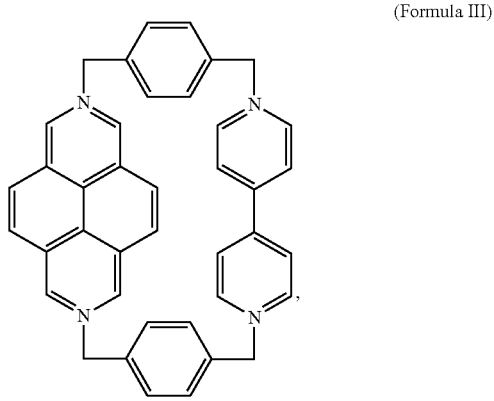

(Formula III)

or a derivative thereof. In some embodiments, the complex comprises a compound of Formula VII,

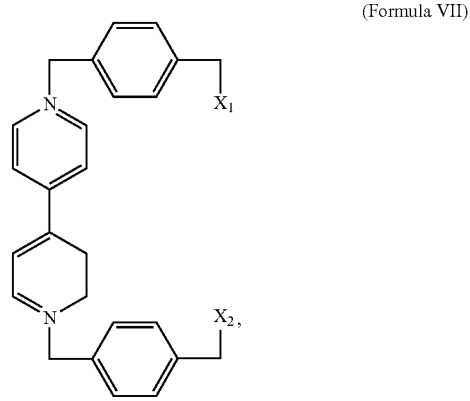

(Formula VII)

or a derivative thereof and wherein $X_1$ and $X_2$ is a halogen.

BRIEF DESCRIPTION OF THE DRAWINGS

FIG. 2A shows a variable scan-rate CV of $MDAP^{2+}$ (1 mM in MeCN, 0.1 M $TBAPF_6$, 298 K) exhibiting an additional oxidation wave at +40 mV upon increasing the scan rate.

FIG. 2B shows UV-Vis-NIR adsorption spectra (50 μM in MeCN, 298 K) of $DB^{·+}$, $DAPQT^{2(·+)}$ and $DB^{·+} \subset DAPQT^{2(·+)}$ indicating the formation of the heterogeneous 1:1 trisradical complex characterized by the appearance of an NIR band centered on 920 nm.

FIG. 2C shows a perspective view of the crystal structure of $(DB \subset DAPQT)^{2·4+}$ showing the torsional angles and plane-to-plane separations.

FIG. 2D shows a side-on view of the solid-state superstructure of $(DB \subset DAPQT)^{2·4+}$ demonstrating the intermolecular interactions.

FIGS. 5A-5C show differential pulse voltammograms of (FIG. 5A) $SC^{·7+}$, (FIG. 5A) $HC^{·7+}$, and (FIG. 5A) $AC^{·7+}$ (1 mM in MeCN, 0.1 M $TBAPF_6$, 200 mV s$^{-1}$, 298 K) showing six reversible redox processes and seven discrete redox states.

FIG. 8B shows UV-Vis-NIR Absorption Spectra (50 μM, MeCN, optical length: 1 cm) of $MDAP^{·+}+CBPQT^{2(·+)}$, $MV^{·+} \subset CBPQT^{2(·+)}$ and $MV^{·+} \subset DAPQT^{2(·+)}$.

FIG. 10A) A perspective view showing the distances between stacked units and the torsional angle of A and B units. FIG. 10B) Space-filling representation. FIG. 10C) A side-on view showing the angle of tilt between the A and B units. FIG. 10D) Part of the solid-state superstructure showing that there are 8 $PF_6$-anions surrounding two 1:1 complexes. Solvent molecules are omitted for the sake of clarity.

FIG. 11A) A perspective view showing the distances between stacked units and torsional angles of A-C units. FIG. 11B) Space-filling representation. FIG. 11C) A side-on view showing the dihedral angle between the B and C units. FIG. 11D) A perspective view showing that there are 7 $PF_6$-anions surrounding the catenane. Solvent molecules are omitted for the sake of clarity.

FIG. 12A) A perspective view showing distances between stacked units and torsional angles of A and B units. FIG. 12B) Space-filling representation. FIG. 12C) A side-on view showing the dihedral angle between the A and B units. FIG. 12D) A perspective view showing that there are 7 $PF_6$-anions surrounding the catenane. Solvent molecules are omitted for the sake of clarity.

DETAILED DESCRIPTION OF THE INVENTION

Figure 1:
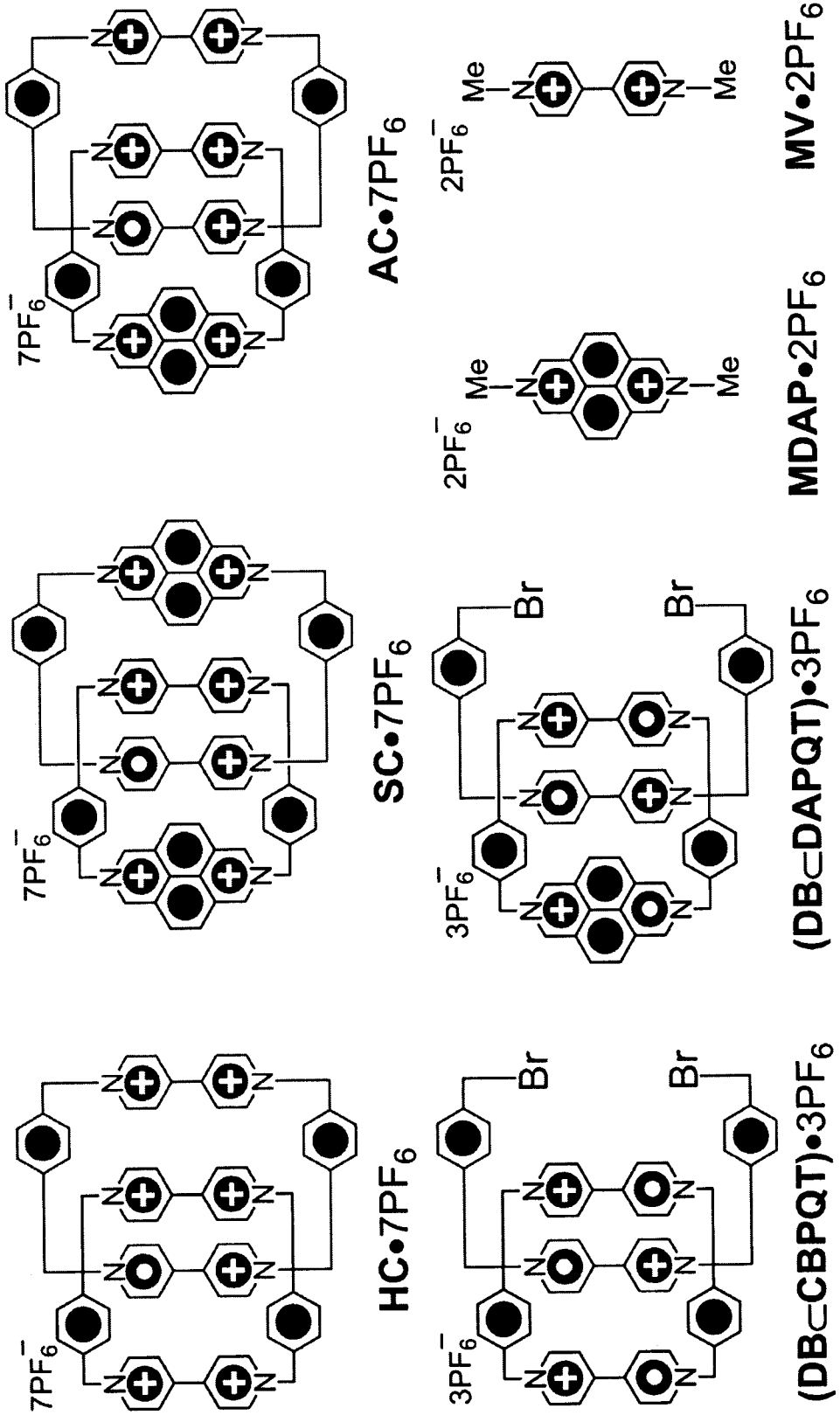
FIG. 1 provides structural formulas of the three radical catenanes $HC.7PF_6$, $SC.7PF_6$ and $AC.7PF_6$ (top), and the 1:1 trisradical tricationic complexes $(DB \subset CBPQT).3PF_6$, $(DB \subset DAPQT).3PF_6$, $MDAP.2PF_6$ and $MV.2PF_6$ (bottom).

Herein we demonstrate a molecular system—namely, a novel class of octacationic [2]catenanes—which exhibits adjustable multiple accessible redox states. We report the radical template-directed syntheses of two analogues (FIG. 1) of $HC^{·7+}$—namely, the asymmetric [2]catenane $AC^{·7+}$ and the symmetric [2]catenane $SC^{\cdot 7+}$—by incorporating simultaneously both the more electron-deficient $BIPY^{2+}$ and the less electron-deficient 2,7-diazapyrenium ($DAP^{2+}$) units into the [2]catenane structures in order to modulate the number of the accessible redox states of the resulting molecules. We show that these [2]catenanes, which exist as persistent air-stable radicals, can exist in a consecutive series of 5 ($SC^{\cdot 7+}$: 0, 4+, 6+, 7+, and 8+), 6 ($HC^{\cdot 7+}$: 0, 2+, 4+, 6+, 7+, and 8+), and 7 ($AC^{\cdot 7+}$: 0, 1+, 2+, 4+, 6+, 7+, and 8+) redox states. We have characterized these mixed-valence and other redox states by (i) electron paramagnetic resonance (EPR) and UV-Vis-NIR spectroscopies, (ii) high-resolution mass spectrometry (HR-MS), (iii) single crystal X-ray diffraction (XRD) analysis, and (iv) electrochemical means.

The molecular systems are catenane compositions. Catenanes are hydrocarbons having two or more macrocyclic rings connected in the manner of links in a chain, without a covalent bond. As demonstrated in the Examples that follow, the catenanes are [2]catenanes having two mechanically interlocked rings.

The first ring and the second ring of the catenane each comprise a 4,4'-bipyridinium (BIPY) subunit or a derivative thereof. An exemplary BIPY subunit is a subunit of Formula I,

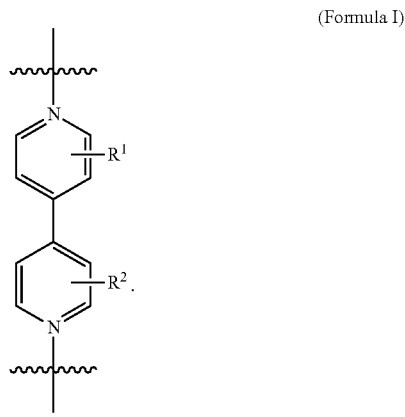

(Formula I)

As disclosed in the examples that follow, the BIPY subunit comprises unsubstituted pyridine groups. Derivatives of the unsubstituted BIPY subunit may be prepared and used to form the catenane compositions described herein by replacing any of the hydrogens on either or both of the pyridine rings with one or more substituents. Exemplary substituents $R^1$ and $R^2$ include, but are not limited to, —$CH_3$, —OH, —$NH_2$, —SH, —CN, —$NO_2$, —F, —Cl, —Br, —I moieties. $R^1$ and $R^2$ may be independently selected. In some instances, $R^1$ and $R^2$ are the same. In other instances, $R^1$ and $R^2$ are the different. Because BIPY subunits are threaded through the opposite macrocyclic ring, the substituents on a threaded BIPY subunit should must be small enough to allow threading. The second ring may further comprise an additional BIPY subunit that is not threaded through the macrocycle of the opposite ring. Because the additional BIPY subunit is not threaded, substituents such as $C_1$-$C_{12}$ alkyl, $C_2$-$C_{12}$ alkenyl, $C_2$-$C_{12}$ alkynyl, $C_1$-$C_{12}$ carboxy, $C_1$-$C_{12}$ carbonyl, $C_1$-$C_{12}$ aldehyde, or $C_1$-$C_{12}$ alkoxy moieties having too much steric bulk to allow threading may also be used for this subunit. In some embodiments, the substituents comprise $C_1$-$C_6$ alkyl, $C_2$-$C_6$ alkenyl, $C_2$-$C_6$ alkynyl, $C_1$-$C_6$ carboxy, $C_1$-$C_6$ carbonyl, $C_1$-$C_6$ aldehyde, or $C_1$-$C_6$ alkoxy moieties or $C_1$-$C_4$ alkyl, $C_2$-$C_4$ alkenyl, $C_2$-$C_4$ alkynyl, $C_1$-$C_4$ carboxy, $C_1$-$C_4$ carbonyl, $C_1$-$C_4$ aldehyde, or $C_1$-$C_4$ alkoxy moieties.

When a ring comprises two BIPY subunits, the BIPY subunits can be the same or different. Both BIPY units may be unsubstituted, one BIPY subunit may be unsubstituted and the other substituted, or both BIPY subunits may be substituted. When both BIPY subunits are substituted, the BIPY subunits may comprise the same or different substituents.

The BIPY subunits may access a number of different redox states, including as a $BIPY^{2+}$ dication or as a $BIPY^{\cdot +}$ radical cation. Formula I may represent the $BIPY^{2+}$, $BIPY^{\cdot +}$, or $BIPY^0$ redox state depending on context. Moreover, when a ring comprises two BIPY subunits, the subunits may be in the same redox state or different redox states. 4,4'-Bipyridinium radical cations ($BIPY^{\cdot +}$) tend to form[6] $(BIPY^{\cdot +})_2$ dimers in a 'face-to-face' manner in the solid state as a result of favorable radical-pairing interactions. Conversely, in a dilute solution, $(BIPY^{\cdot +})_2$ dimers are prone[7] to dissociate because of their low association constants.

The first ring also comprises a 2,7-diazapyrenium (DAP) subunit or a derivative thereof. An exemplary DAP subunit is subunit of Formula II,

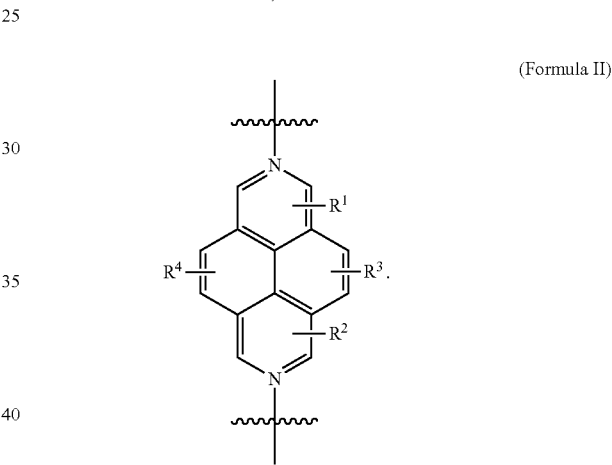

(Formula II)

As disclosed in the examples that follow, the DAP subunit comprises a unsubstituted 2,7-diazapyrenium group. Derivatives of the unsubstituted DAP subunit may be prepared and used to form the catenane compositions described herein by replacing any of the hydrogens on any or all of the rings with one or more substituents. Exemplary substituents $R^1$, $R^2$, $R^3$, and $R^4$ include, but are not limited to, alkyl, alkenyl, alkynyl, carboxy, carbonyl, aldehyde, alkoxy, —OH, —$NH_2$, —SH, —CN, —$NO_2$, —F, —Cl, —Br, —I moieties. $R^1$, $R^2$, $R^3$, and $R^4$ may be independently selected. In some instances, $R^1$, $R^2$, $R^3$, and $R^4$ are the same, $R^1$ and $R^2$ are the same, or $R^3$ and $R^4$ are the same. In other instances, $R^1$, $R^2$, $R^3$, and $R^4$ are all different. Because a DAP subunit may be sterically hindered from threading through the opposite macrocyclic ring, the DAP subunit may also include larger substituents than a threaded BIPY. This allows for the use of $C_1$-$C_{12}$ alkyl, $C_1$-$C_{12}$ alkenyl, $C_1$-$C_{12}$ alkynyl, $C_1$-$C_{12}$ carboxy, $C_1$-$C_{12}$ carbonyl, $C_1$-$C_{12}$ aldehyde, or $C_1$-$C_{12}$ alkoxy moieties, for example. In some embodiments, the substituents comprise $C_1$-$C_6$ alkyl, $C_1$-$C_6$ alkenyl, $C_1$-$C_6$ alkynyl, $C_1$-$C_6$ carboxy, $C_1$-$C_6$ carbonyl, $C_1$-$C_6$ aldehyde, or $C_1$-$C_6$ alkoxy moieties or $C_1$-$C_4$ alkyl, $C_1$-$C_4$ alkenyl, $C_1$-$C_4$ alkynyl, $C_1$-$C_4$ carboxy, $C_1$-$C_4$ carbonyl, $C_1$-$C_4$ aldehyde, or $C_1$-$C_4$ alkoxy moieties.

The DAP subunits may access a number of different redox states, including as a DAP$^{2+}$ dication or as a DAP$^{\cdot+}$ radical cation. Formula II may represent the DAP$^{2+}$, DAP$^{\cdot+}$, or DAP$^0$ redox state depending on context. The redox properties of the N,N'-dimethyl-2,7-diazapyrenium dication (MDAP$^{2+}$) were explored by variable scan-rate cyclic voltammetry (CV) and compared with those of 1,1'-dimethyl-4,4'-bipyridinium (MV$^{2+}$). CV of MDAP$^{2+}$ at 10 mV s$^{-1}$ reveals (FIG. 2A, black trace) that the reduction of MDAP$^{2+}$ to MDAP$^{\cdot+}$ occurs at a potential of −450 mV, which is similar to that of 480 mV for MV$^{2+}$. As the scan rate is increased, the reduction wave remains the same, but the intensity of the original oxidation wave at −370 mV gradually decreases, and meanwhile a new oxidation wave appears at +40 mV. Eventually, at the scan rate of 1 V s$^{-1}$ (FIG. 2A, purple trace), two oxidation waves reach the same intensity. These observations indicate that, in solution, the MDAP$^{\cdot+}$ radical cations exist primarily as cationic radical dimers (MDAP$^{\cdot+}$)$_2$, wherein oxidation leads firstly to the formation of a single unpaired spin mixed-valence dimer (MDAP$_2$)$^{\cdot3+}$ before it completely dissociates into two MDAP$^{2+}$ dications. It is also possible that the MDAP$^{\cdot+}$ radical cation forms oliogomers in addition to dimer.

When the scan rate is slower than the time scale of the dissociation of (MDAP$_2$)$^{\cdot3+}$, oxidation of (MDAP$^{\cdot+}$)$_2$ is observed to occur as a single oxidation wave. Once the scan rate becomes faster than the dissociation rate, however, two separate oxidation waves corresponding to (MDAP$^{\cdot+}$)$_2$→(MDAP$_2$)$^{\cdot3+}$ and (MDAP$_2$)$^{\cdot3+}$→2 MDAP$^{2+}$ can be observed. In contrast to MDAP$^{\cdot+}$, the MV$^{\cdot+}$ radical cations exist mainly as monomers. It can be concluded that, in addition to radical pairing interactions, the (MDAP$^{\cdot+}$)$_2$ dimers are most likely further stabilized[14] by additional [π . . . π] interactions between the large aromatic π-surfaces of MDAP$^{\cdot+}$.

An exemplary embodiment of the first ring is the compound of Formula III (DAPQT),

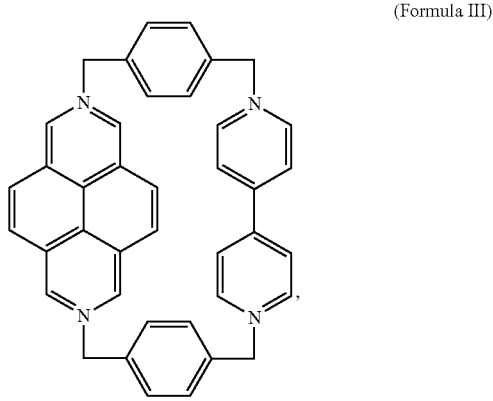

(Formula III)

Derivatives may also be prepared by substituting any of the hydrogens on any of the aromatic rings of the BIPY or DAP subunits as described above. The phenylene subunits may be similarly substituted. Exemplary substituents for any of the rings of Formula III include, but are not limited to, alkyl, alkenyl, alkynyl, carboxy, carbonyl, aldehyde, alkoxy, —OH, —NH$_2$, —SH, —CN, —NO$_2$, —F, —Cl, —Br, or —I moieties.

The compound of formula III may access a number of different redox states due to the BIPY and DAP subunits, including a tetracationic state, a radical tricationic state, or a diradical dicationic state. Formula III may represent any accessible redox state depending on context.

An exemplary embodiment of the second ring is the compound of Formula III or a derivative thereof. The first ring and the second ring may be different derivatives of Formula III.

Another exemplary embodiment of the second ring is a compound of Formula IV (CBPQT),

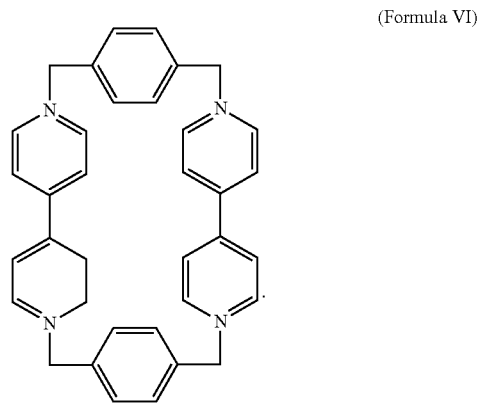

(Formula VI)

Derivatives may also be prepared by substituting any of the hydrogens on any of the aromatic rings of the BIPY subunit as described above. The phenylene subunits may be similarly substituted. There are many substituents that may be used to replace the hydrogen atoms. Exemplary substituents for any of the rings of Formula IV include, but are not limited to, alkyl, alkenyl, alkynyl, carboxy, carbonyl, aldehyde, alkoxy, —OH, —NH$_2$, —SH, —CN, —NO$_2$, —F, —Cl, —Br, —I moieties.

The compound of formula IV may access a number of different redox states due to the BIPY subunits, including a tetracationic state, a radical tricationic state, and a diradical dicationic state. Formula IV may represent any accessible redox states depending on context.

In a specific embodiment, the [2]catenane composition comprises two mechanically interlocked rings of Formula III. The resulting, symmetric catenane (SC) is a composition of Formula V,

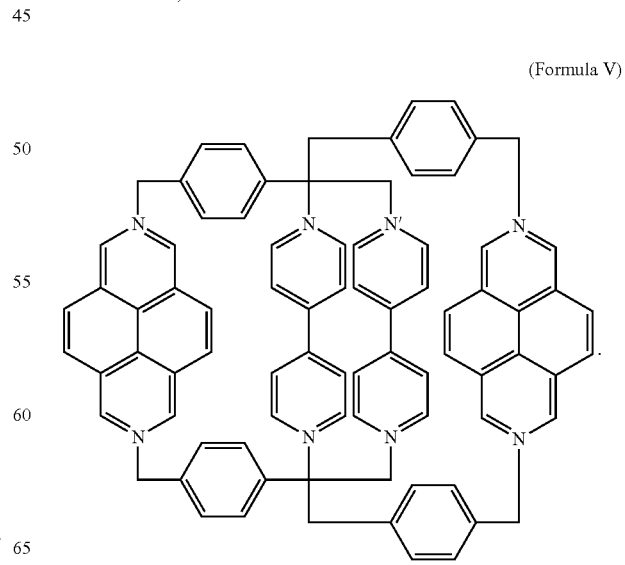

(Formula V)

Derivatives may also be prepared from substituted BIPY subunits, substituted DAP subunits, and/or substituted phenylene subunits as described above.

In a specific embodiment, the [2]catenane composition comprises two mechanically interlocked rings of Formula III and Formula IV. The resulting, antisymmetric catenane (AC) is a composition of Formula VI,

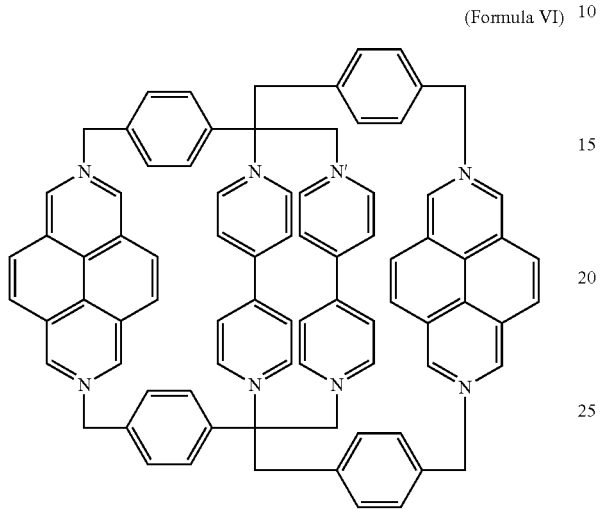

(Formula VI)

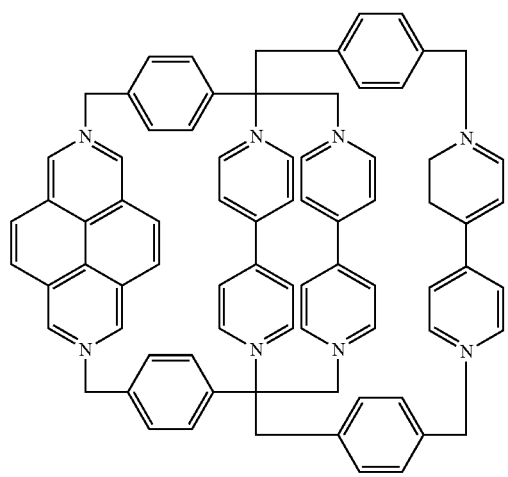

Derivatives may also be prepared from substituted BIPY subunits, substituted DAP subunits, and/or substituted phenylene subunits as described above.

The mechanically interlocked compositions may be prepared by providing a radical cationic inclusion complex and reacting the complex with 2,7-diazapyrene, 4,4'-bipyridine, or derivative of either the diazapyrene or bipyridine compounds, wherein the complex comprises a ring comprising a 4,4'-bipyridinium subunit or a derivative thereof and a diazapyrenium subunit or a derivative thereof. The complex may be provided by contacting the ring and a compound comprising a 4,4'-bipyridinium subunit or a derivative thereof under appropriate conditions.

In an exemplary embodiment, the compound comprising a 4,4'-bipyridinium subunit is a compound of Formula VII,

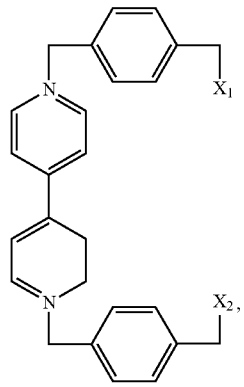

(Formula VII)

$X_1$ and $X_2$ may be any halogen, including Br. Derivatives may also be prepared from substituted BIPY subunits as described above.

Cyclobis(paraquat-p-phenylene) bisradical dication ($CBPQT^{2(\cdot+)}$) and a $BIPY^{\cdot+}$ radical cation are capable of assembling to afford a stable trisradical tricationic inclusion complex $BIPY^{\cdot+} \subset CBPQT^{2(\cdot+)}$ in MeCN, assisted by radical-pairing interactions. [See, e.g., U.S. Pat. No. 9,120,799 to Fahrenbach et al, Fahrenbach et al. J. Am. Chem. Soc. 2012, 134, 3061, and Barnes et al., *Science* 2013, 339, 429 (each incorporated herein in their entirety for all purposes).] This 1:1 inclusion complex may be employed in recognition motifs, either to template[9] the formation of, otherwise difficult to synthesize highly energetic mechanically interlocked molecules (MIMs), or to enhance[10] the switching performance of bistable MIMs. In particular, we have been able to synthesize[9] (FIG. 1) an air- and water-stable paramagnetic homo[2]catenane $HC^{.7+}$ from the trisradical complex $DB^{\cdot+} \subset CBPQT^{2(\cdot+)}$. Up to six redox states of this [2]catenane can be accessed electrochemically.

Upon reducing[15] an equimolar mixture of a 1,1'-disubstituted 4,4'-bipyridinium salt ($DB.2PF_6$) and $DAPQT.4PF_6$ in MeCN, a purple solution was obtained. Its UV-Vis-NIR spectrum exhibits (FIG. 2B) an absorption band centered on 920 nm, which is characteristic of radical cationic $(BIPY^{\cdot+})_2$ dimers.[14] This observation implies that the $DAP^{\cdot+}$ unit in $DAPQT^{2(\cdot+)}$ interacts with the $DB^{\cdot+}$ radical cation very weakly if at all and the radical-pairing interaction is mainly associated with the interaction between the two $BIPY^{\cdot+}$ units and the $DB^{\cdot+}$ radical cation. The association constant ($K_a$) of $DB^{\cdot+} \subset DAPQT^{2(\cdot+)}$ was determined to be $(8.9 \pm 5.5) \times 10^3$ $M^{-1}$ in MeCN by UV-Vis-NIR titration. It is [8] lower than the one ($K_a = 5.0 \times 10^4$ $M^{-1}$) observed for $DB^{\cdot+} \subset CBPQT^{2(\cdot+)}$, suggesting that the DAP' unit does not interact strongly with $DB^{\cdot+}$. An attempt to form the hetero trisradical tricationic complex $MDAP^{\cdot+} \subset CBPQT^{2(\cdot+)}$ was not successful as indicated by the absence of a NIR absorption band in its UV-Vis-NIR spectrum. This failure to form a 1:1 inclusion complex reflects the fact that the cavity of $CBPQT^{2(\cdot+)}$ is not large enough to accommodate $MDAP^{\cdot+}$.

Single crystals of a 1:1 inclusion complex which does form were obtained by slow vapor diffusion of $^iPr_2O$ into an MeCN solution of an equimolar mixture of $DB^{\cdot+}$ and $DAPQT^{2(\cdot+)}$ in an Ar-filled glovebox. The solid-state superstructure (FIGS. 2C and 10A-10D) reveals that each inclusion complex is surrounded by four $PF_6^-$-counterions, an observation which indicates that the complex is indeed the bisradical tetracation (($DB \subset DAPQT)^{2.4+}$) rather than a trisradical trication in the solid state. The bisradical tetracationic state could be the result of partial oxidation during crystallization, especially since the DAP$^{\cdot+}$ radical cation does not interact efficiently with DB$^{\cdot+}$[15]. Such a situation has also been observed in several other systems. Since the torsional angles of both units A and B are less than 3° and the plane-to-plane separation between them is only 3.1 Å, the implication is that both units A and B are in the radical cationic BIPY$^{\cdot+}$ state and the remaining unit C is in the dicationic DAP$^{2+}$ state. The plane-to-plane separation between units B and C is 3.4 Å, a distance which is a typical one for [π . . . π] interactions. In addition, the complex is further stabilized by multiple [C—H . . . π] interactions between the p-phenylene rings on the unit A and C—H groups on the DAP$^{2+}$ unit. Overall, the superstructure is arranged (FIG. 2D) in an infinite stack, driven by intermolecular [Br . . . π] interactions between adjacent inclusion complexes.

Figure 13:
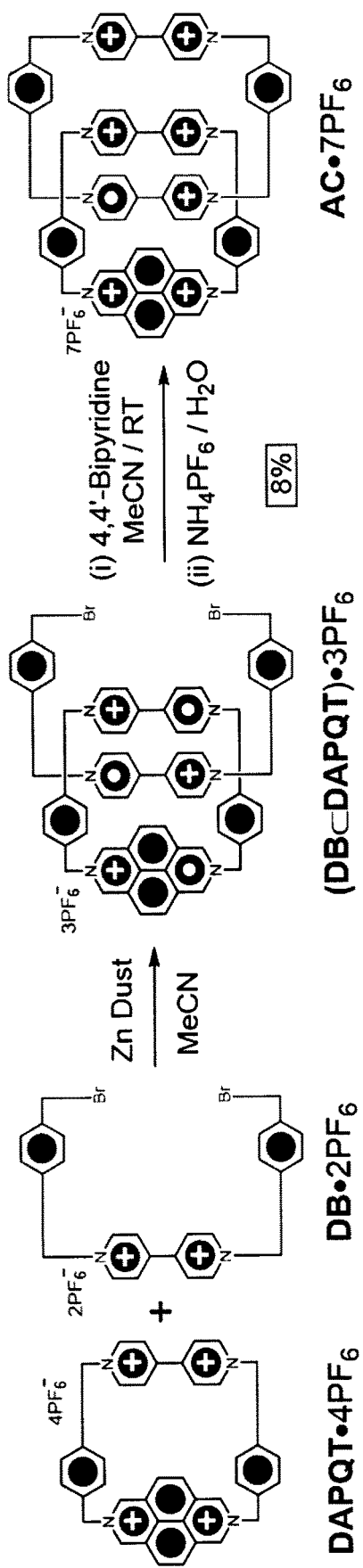
FIG. 13 illustrates synthetic schemes for preparing [2]Catenane $AC.7PF_6$ (Scheme 1) and [2]Catenane $SC.7PF_6$ (Scheme 2).
Figure 13:
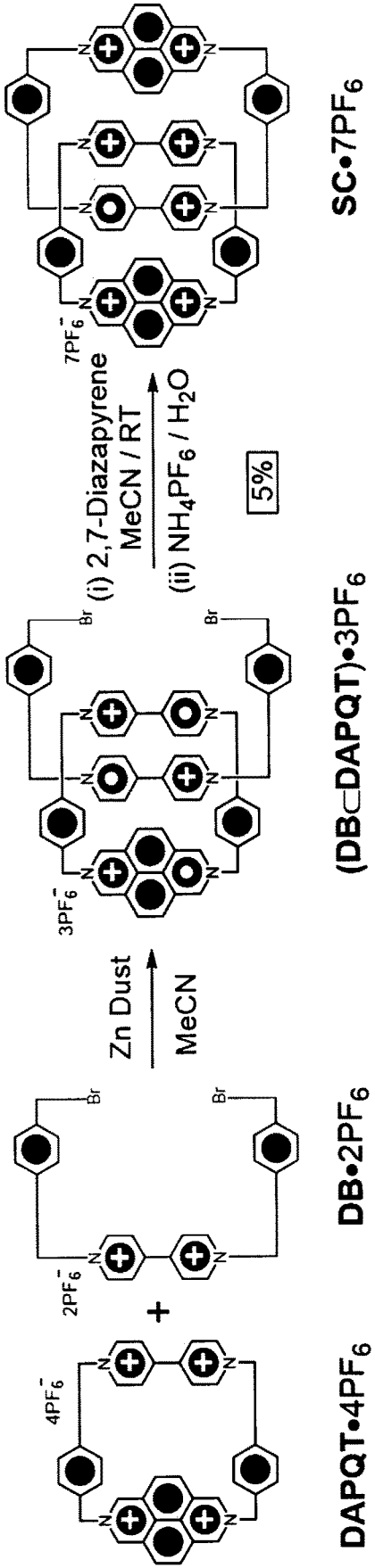

Since the hetero trisradical tricationic complex is stable in MeCN, we synthesized AC.7PF$_6$ and SC.7PF$_6$ according to Schemes 1 and 2 (FIG. 13).

Figure 3:
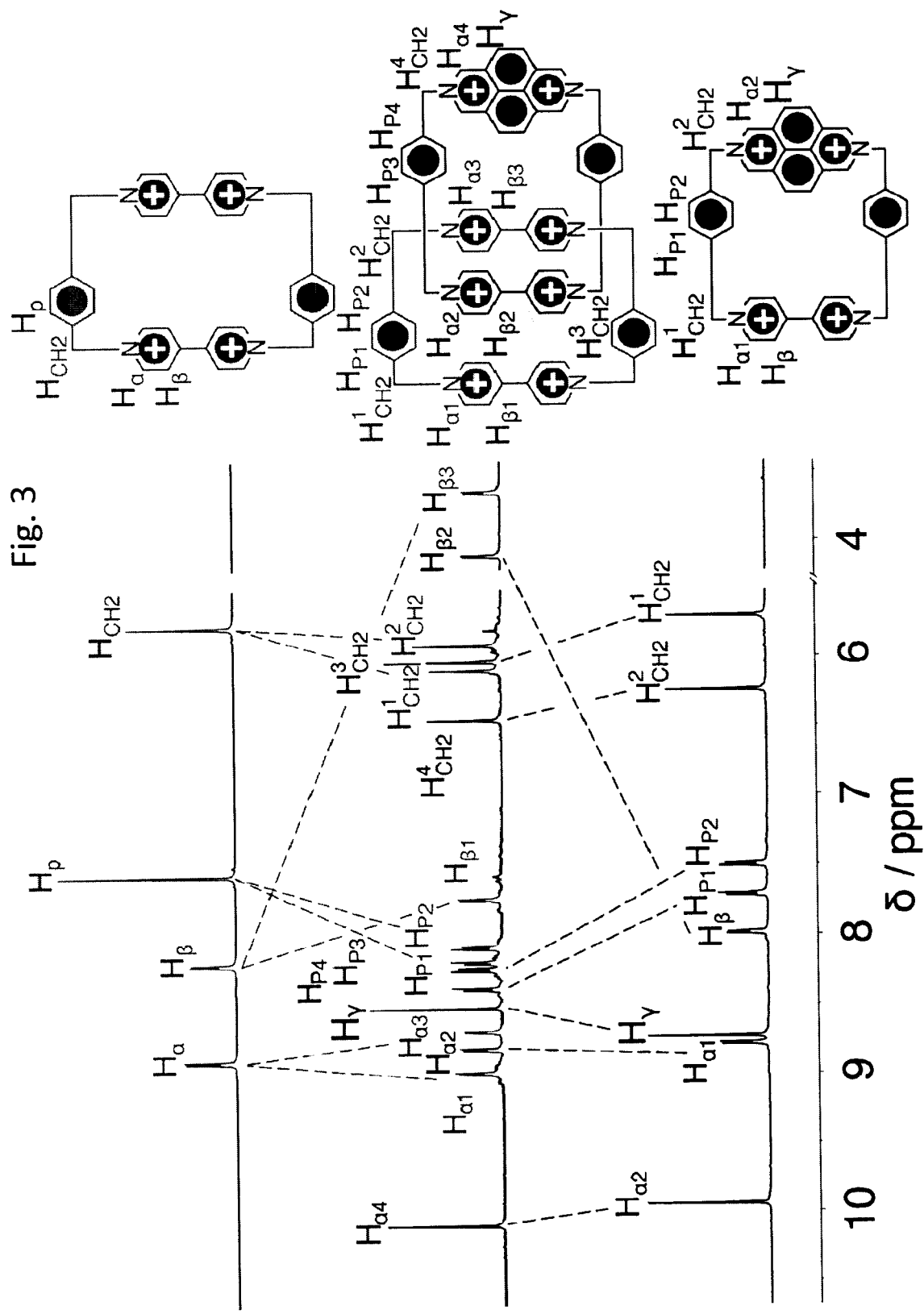
FIG. 3 shows a comparison of $^1H$ NMR spectra (500 MHz, $CD_3CN$, 298 K) of (top) $CBPQT^{4+}$, (middle) $AC^{8+}$ and (bottom) $DAPQT^{4+}$.
Figure 7A:
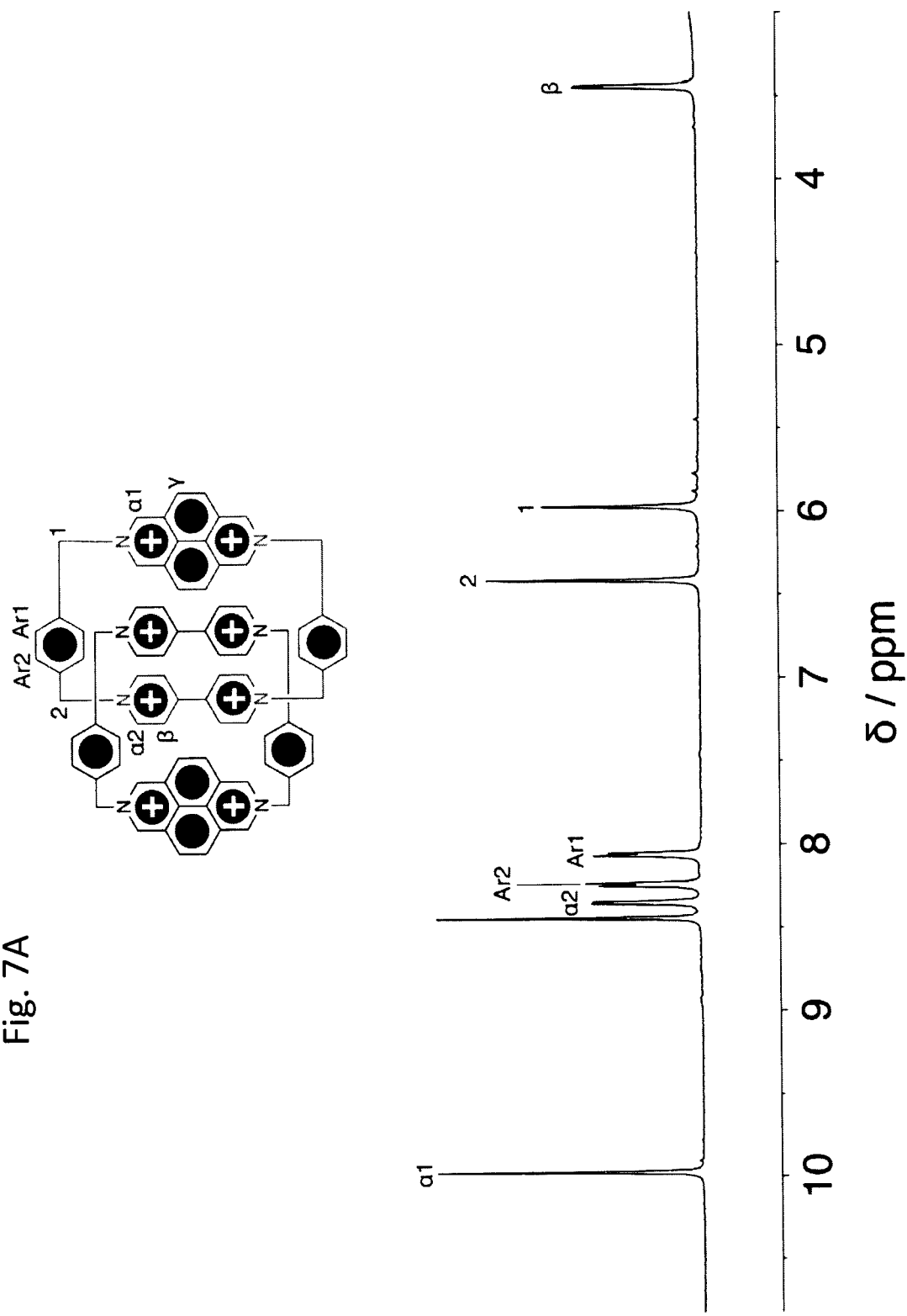
FIG. 7A shows a $^1H$ NMR Spectrum (500 MHz, $CD_3CN$, 298 K) of $SC.8PF_6$.
Figure 7B:
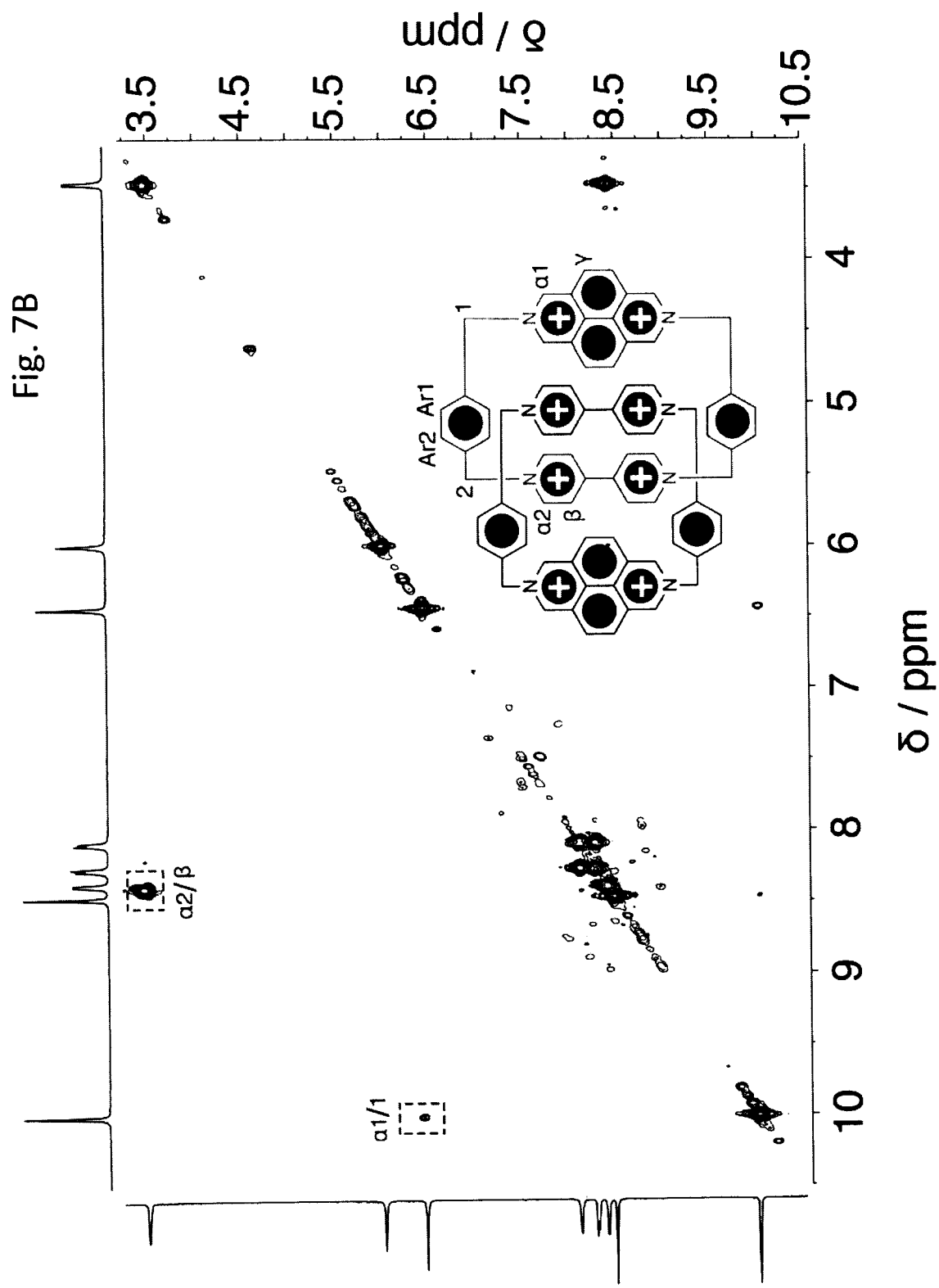
FIG. 7B shows a $^1H$-$^1H$ gCOSY NMR Spectrum (500 MHz, $CD_3CN$, 298 K) of $SC.8PF_6$.

The in situ formed complex DE$^{\cdot+}$⊂DAPQT$^{2(\cdot+)}$ was allowed to react with 4,4'-bipyridine and 2,7-diazapyrene, respectively, for two weeks at room temperature to afford both AC.7PF$_6$ and SC.7PF$_6$ as purple solids. The $^1$H NMR spectra of both catenanes were obtained for their fully oxidized states AC.8PF$_6$ and SC.8PF$_6$ which were prepared by oxidizing the as-synthesized catenanes with an excess of NO.PF$_6$. AC$^{8+}$ possesses a time-averaged C$_{2v}$ symmetry and hence displays (FIG. 3B) a relatively complicated $^1$H NMR spectrum on account of the interlock-induced desymmetrization. It is worth highlighting that the proton resonances for H$_{β2}$ and H$_{β3}$, belonging to the two innermost BIPY$^{2+}$ units are shifted dramatically upfield by 3.9 and 4.6 ppm because of the strong shielding effect imposed by their accompanying cyclophanes. The slightly larger upfield shift observed for H$_{β3}$ is ascribed to the stronger shielding effect on H$_{β3}$ exerted by the DAP$^{2+}$ unit on DAPQT$^{4+}$. SC$^{8+}$, which has a higher time-averaged D$_{2d}$ symmetry, exhibits (FIG. 7A) a comparatively simple $^1$H NMR spectrum and is also characterized by the upfield shifted H$_β$.

Figure 4C:
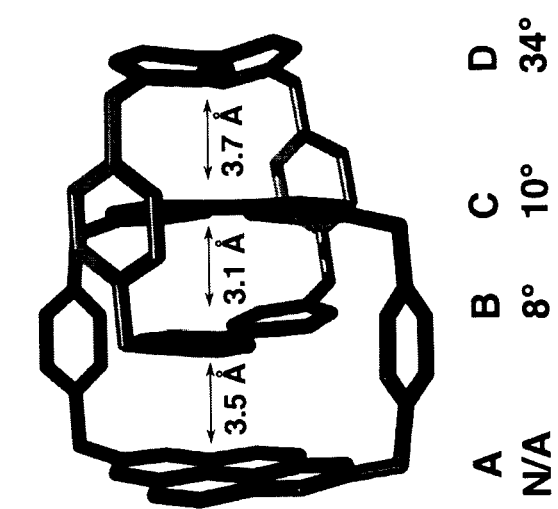
FIG. 4C shows a perspective views of X-ray crystal structures of $AC^{·7+}$ highlighting its torsional angles and plane-to-plane separations.
Figure 4D:
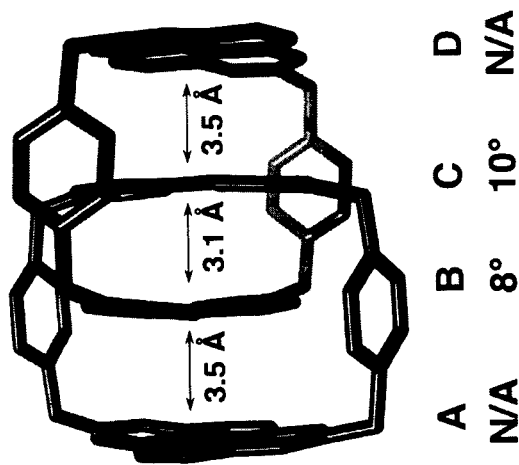
FIG. 4D shows perspective views of X-ray crystal structures of $SC^{·7+}$ highlighting its torsional angles and plane-to-plane separations.
Figure 4A:
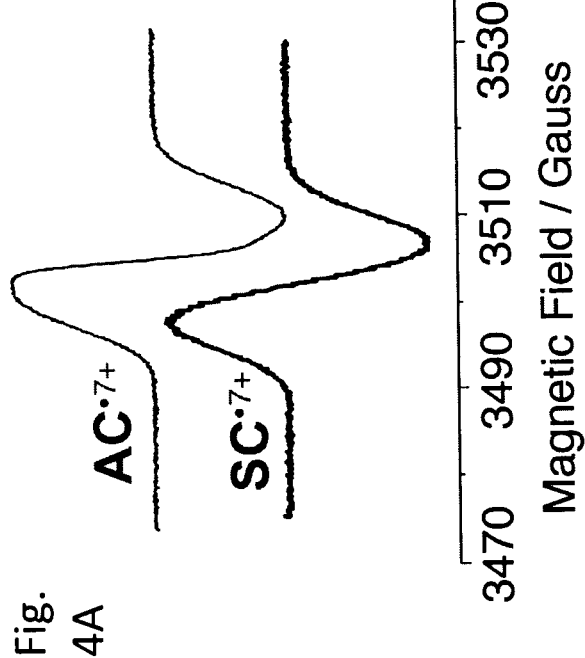
FIG. 4A shows EPR spectra of $AC^{·7+}$ and $SC^{·7+}$ (0.2 mM in MeCN, 298 K) displaying indiscernible hyperfine splitting patterns.
Figure 4B:
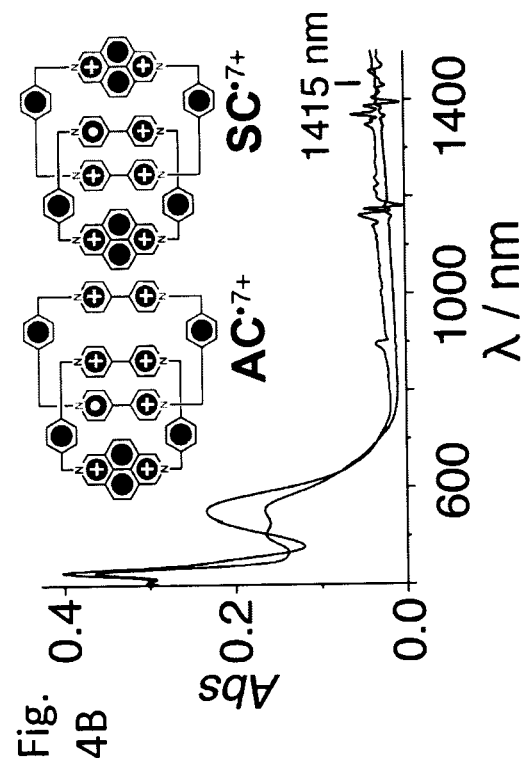
FIG. 4B shows UV-Vis-NIR absorption spectra (50 μM in MeCN, 298 K) of $AC^{·7+}$ and $SC^{·7+}$, both showing a broad NIR absorption band centered on 1415 nm.

In order to confirm beyond any doubt that the as-synthesized catenanes exist as persistent stable radicals, we performed EPR measurements. The results reveal (FIG. 4A) that both catenanes are EPR active, an observation which is in good agreement with their containing an unpaired electron. Moreover, the spectra display indiscernible hyperfine splitting, an observation which suggests that rapid spin exchange exists within both catenanes. This conclusion is also supported[16] (FIG. 4B) by the NIR absorption bands centered on ca. 1415 nm in their UV-Vis-NIR spectra.

In order to gain more insight into the location of the delocalized radical electron, single crystal XRD analyses were performed on single crystals of AC.7PF$_6$ and SC.7PF$_6$. The crystals have a molecular packing arrangement defined by the triclinic space group P$\bar{1}$ (no. 2). AC.7PF$_6$ has lattice parameters of a=13.5±0.1 Å, b=16.5±0.1 Å, c=22.5±0.1 Å, α=86.1±0.1°, β=88.9±0.1°, γ=82.5±0.1°. AC.7PF$_6$ has lattice parameters of a=13.3±0.1 Å, b=27.9±0.1 Å, c=31.5±0.1 Å, α=73.4±0.1°, β=89.8±0.1°, γ=81.0±0.1°. The solid-state structures demonstrate (FIGS. 4C, 4D, 11A-11D, and 12A-12D) that each catenane crystallizes with 7 PF$_6$-counterions, an observation which is consistent with their mono-radical states. In the case of AC$^{\cdot7+}$, the torsional angle of 34° for the unit D, is typical for the dicationic BIPY$^{2+}$ unit and tells us that the unpaired electron is not located on the unit D. By contrast, units B and C have smaller torsional angles— namely, 8° and 10°, respectively—and thus the heterocyclic rings can be deemed as being almost coplanar. The flattening effect suggests that the unpaired electron is shared by units B and C. This conclusion is further supported by their short plane-to-plane separation, which is only 3.1 Å being typical for single unpaired spin interactions[9]. The large plane-to-plane separation (3.5 Å) between units A and B suggests that the unit A is unlikely to be involved in the electron sharing. In the same manner, it can be argued that the unpaired electron in SC$^{\cdot7+}$ is shared by units B (8°) and C (10°) as well. Along with the observations for HC$^{\cdot7+}$, it can be concluded that the change from BIPY$^{2+}$ to DAP$^{2+}$ does not affect the location of the unpaired electrons.

Differential pulse voltammetry (DPV) reveals that AC$^{\cdot7+}$ exhibits (FIG. 5C) up to six redox processes and as many as seven discrete accessible redox states on account of its low symmetry, whereas SC$^{\cdot7+}$ has (FIG. 5A) only four redox processes and five redox states. In contrast, there are five redox processes and six redox states in the differential pulse voltammogram (FIG. 5B) of HC.7PF$_6$. These observations indicate the fact that the introduction of the less electron-deficient DAP$^{2+}$ units to replace the BIPY$^{2+}$ units can precisely modulate the stereoelectronic effect in this octacationic [2]catenane system. As a consequence, a consecutive series of five, six, and seven redox states are achieved in the resulting SC.7PF$_6$ (0, 4+, 6+, 7+, and 8+), HC.7PF$_6$ (0, 2+, 4+, 6+, 7+, and 8+), and AC.7PF$_6$ (0, 1+, 2+, 4+, 6+, 7+, and 8+), respectively, which render these catenanes ideal for applications as memory devices. In particular, all these redox states can be accessed at low potentials, ranging from −1.1 to +0.5 V, which guarantee very low write and erase voltages. As such, these three catenanes may be used to create high-density memory devices with low energy consumption.

Considerable efforts have been devoted to developing multilevel memories in order to increase data density. One effective way is to utilize a collection of redox-active molecules wherein information can be stored in discrete redox states. Multilevel memories of this type are described in Busche, C. et al., *Nature* 2014, 515, 545 and Liu, Z. et al., *J. Mater. Chem. C* 2015, 3, 2033. As a result, increasing the number of redox states within a single molecule can potentially help to realize the high density data storage.

Definitions

As used herein, an asterick "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C$_1$-C$_{12}$ alkyl, C$_1$-C$_{10}$-alkyl, and C$_1$-C$_6$-alkyl, respectively.

The term "alkylene" refers to a diradical of an alkyl group. An exemplary alkylene group is —CH$_2$CH$_2$—.

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, and the like The term "heteroalkyl" as used herein refers to an "alkyl" group in which at least one carbon atom has been replaced with a heteroatom (e.g., an O, N, or S atom). One type of heteroalkyl group is an "alkoxyl" group The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$-alkenyl, $C_2$-$C_{10}$-alkenyl, and $C_2$-$C_6$-alkenyl, respectively The term "alkynyl" as used herein refers to an unsaturated straight or branched hydrocarbon having at least one carbon-carbon triple bond, such as a straight or branched group of 2-12, 2-10, or 2-6 carbon atoms, referred to herein as $C_2$-$C_{12}$-alkynyl, $C_2$-$C_{10}$-alkynyl, and $C_2$-$C_6$-alkynyl, respectively The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a diradical of an cycloalkyl group.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a $C_3$-$C_7$ heterocyclyl group refers to a saturated or partially unsaturated 3- to 7-membered ring structure containing one to four heteroatoms, such as nitrogen, oxygen, and sulfur. The designation "$C_3$-$C_7$" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines, wherein substituents may include, for example, alkyl, cycloalkyl, heterocyclyl, alkenyl, and aryl.

The terms "alkoxyl" or "alkoxy" are art-recognized and refer to an alkyl group, as defined above, having an oxygen radical attached thereto. Representative alkoxyl groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

An "epoxide" is a cyclic ether with a three-atom ring typically include two carbon atoms and whose shape approximates an isosceles triangle. Epoxides can be formed by oxidation of a double bound where the carbon atoms of the double bond form an epoxide with an oxygen atom. The term "carbonyl" as used herein refers to the radical —C(O)—.

The term "carboxamido" as used herein refers to the radical —C(O)NRR', where R and R' may be the same or different. R and R' may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" as used herein refers to a radical of the form $R^1C(O)N(R^2)$—, —$R^1C(O)N(R^2)R^3$—, —$C(O)NR^2R^3$, or —$C(O)NH_2$, wherein $R^1$, $R^2$ and $R^3$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

Miscellaneous

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

General Methods

All reagents were purchased from commercial suppliers and used without further purification. Compounds MDAP.2PF$_6$, DB.2PF$_6$, CBPQT.4PF$_6$, and DAPQT.4PF$_6$ were prepared[Ashton, P. R et al., New J. Chem. 1999, 23, 587; Barnes, J. C. et al. J. Org. Chem. 2013, 78, 11962-11969.] according to literature procedures. Thin layer chromatography (TLC) was performed on silica gel 60 F254 (E. Merck). Column chromatography was carried out on silica gel 60F (Merck 9385, 0.040-0.063 mm). C-18 Columns were used for analytical and preparative reverse-phase high-performance liquid-chromatography (RP-HPLC) on Agilent 1260 infinity LC equipped with Agilent 6120 LC/MS electrospray system and Shimadzu Prominence LC-8a instruments, respectively, eluted with H$_2$O/MeCN (0.1% v/v TFA) and monitored using a UV detector ($\lambda$=360 nm). UV/Vis Spectra were recorded at room temperature on a Shimadzu UV-3600 spectrophotometer. Nuclear magnetic resonance (NMR) spectra were recorded on Agilent DD2 500 as well as on Bruker Avance III 400 and 500 spectrometers, with working frequencies of 400 and 500 MHz for $^1$H, as well as 100 and 125 MHz for $^{13}$C nuclei, respectively. Chemical shifts were reported in ppm relative to the signals corresponding to the residual non-deuterated solvents (CD$_3$CN: $\delta_H$=1.94 ppm and $\delta_C$=118.26 ppm for $^{13}$CN). High-resolution mass spectra (HR-ESI) were measured on a Finnigan LCQ iontrap mass spectrometer. Electron paramagnetic resonance (EPR) measurements at X-band (9.5 GHz) were performed with a Bruker Elexsys E580, equipped with a variable Q dielectric resonator (ER-4118X-MD5-W1). All samples were prepared in an Argon-filled atmosphere. Samples were loaded into quartz 1.4 mm tubes and sealed with a clear ridged UV doming epoxy (IllumaBond 60-7160RCL) and used immediately after preparation. Cyclic voltammetry (CV) and differential pulse voltammetry (DPV) experiments were carried out at room temperature in argon-purged MeCN solutions with a Gamry Multipurpose instrument (Reference 600) interfaced to a PC. CV Experiments were performed using a glassy carbon working electrode (0.071 cm$^2$). The electrode surface was polished routinely with 0.05 μm alumina-water slurry on a felt surface immediately before use. The counter electrode was a Pt coil and the reference electrode was Ag/AgCl electrode. The concentration of the supporting electrolyte tetrabutylammonium hexafluorophosphate (NH$_4$PF$_6$) was 0.1 M.

Synthesis of the [2]Catenane AC.7PF$_6$

AC.7PF$_6$ was prepared according to Scheme 1. DAPQT.4PF$_6$ (432 mg, 0.38 mmol) and DB.2PF$_6$ (306 mg, 0.38 mmol) were dissolved in degassed MeCN (140 mL) in a 250-mL round-bottomed flask in a glovebox. An excess of Zn dust (~100 mg) was added under vigorous stirring to this solution. After 30 min, the solution turned from colorless to a deep purple color, an observation which is indicative of the formation of the hetero-trisradical complex (DB⊂DAPQT).3PF$_6$. The excess of Zn dust was filtered off. The purple filtrate was collected in another round-bottomed flask and 4,4'-bipyridine (62 mg, 0.40 mmol) was added to it. The resulting mixture was allowed to stand for 2 weeks at room temperature before being removed from the glovebox and the solvent evaporated off under vacuum. The resulting deep purple solid was subjected to RP-HPLC (H$_2$O/MeCN 0.1% TFA/0→100% in 40 min). Pure fractions were collected, concentrated, added to a saturated NH$_4$PF$_6$ solution (ca. 20 mL), and filtered to afford AC.7PF$_6$ as a purple solid (59 mg, 8%). For NMR spectroscopic characterization, AC.7PF$_6$ (2 mg) was oxidized to AC.8PF$_6$ by the addition of an excess (1 mg) of NO.PF$_6$. $^1$H NMR (500 MHz, CD$_3$CN, 298 K) of AC.8PF$_6$: $\delta_H$=10.06 (s, 4H), 8.96 (d, J=6.7 Hz, 4H), 8.78 (d, J=6.7 Hz, 4H), 8.66 (d, J=7.1 Hz, 4H), 8.49 (s, 4H), 8.35 (d, J=8.4 Hz, 4H), 8.21 (d, J=8.3 Hz, 4H), 8.16 (d, J=8.3 Hz, 4H), 8.05 (d, J=8.3 Hz, 4H), 7.71 (d, J=6.7 Hz, 4H), 6.42 (s, 4H), 6.07 (s, 4H), 5.89 (s, 4H), 4.08 (d, J=6.7 Hz, 4H), 3.62 (d, J=6.7 Hz, 4H). $^{13}$C NMR (125 MHz, CD$_3$CN, 298 K) of AC.8PF$_6$: $\delta_C$=148.7, 148.1, 142.9, 141.9, 140.3, 140.0, 138.5, 138.2, 132.9, 132.8, 132.3, 132.1, 131.8, 131.3, 130.1, 128.5, 128.3, 128.1, 122.3, 121.6, 67.8, 67.3, 67.2, 65.7, 65.3, 65.1, 63.4, 48.0, 36.9, 32.6, 31.7, 30.9, 30.3, 30.1, 29.8, 23.4, 22.9, 14.4, 9.2. ESI-HRMS for AC.7PF$_6$; Calcd for C$_{76}$H$_{64}$F$_{42}$N$_8$P$_7$: m/z=1958.3099 [M-PF$_6$]$^+$; found: 1958.3109.

Synthesis of the [2]Catenane SC.7PF$_6$

SC.7PF$_6$ was prepared according to Scheme 2. Following a procedure similar to that described for the synthesis of AC.7PF$_6$, the reaction of a mixture composed of DAPQT.4PF$_6$ (200 mg, 0.17 mmol), DB.2PF$_6$ (142 mg, 0.17 mmol) and 2,7-diazapyrene (36 mg, 0.17 mmol) afforded SC.7PF$_6$ as a purple solid (18 mg, 5%). For NMR spectroscopic characterization, SC.7PF$_6$ (2 mg) was oxidized to SC.8PF$_6$ by the addition of an excess (1 mg) of NO.PF6. $^1$H NMR (500 MHz, CD$_3$CN, 298 K) of SC.8PF$_6$: $\delta_H$=9.97 (s, 8H), 8.44 (s, 8H), 8.35 (d, J=5.8 Hz, 8H), 8.24 (d, J=7.8 Hz, 8H), 8.06 (d, J=7.8 Hz, 8H), 6.41 (s, 8H), 5.97 (s, 8H), 3.45 (d, J=5.8 Hz, 8H). $^{13}$C NMR (125 MHz, CD$_3$CN, 298 K) of SC.8PF$_6$: $\delta_C$=147.9, 144.1, 141.9, 141.6, 138.3, 132.9, 132.1, 131.7, 130.0, 126.2, 121.5, 67.7, 31.0. ESI-HRMS for SC.7PF$_6$; Calcd for C$_{80}$H$_{64}$F$_{36}$N$_8$P$_6$: m/z=2006.3099 [M-PF$_6$]$^+$; found: 2006.3102.

$^1$H NMR Spectra of AC.8PF$_6$

Figure 6A:
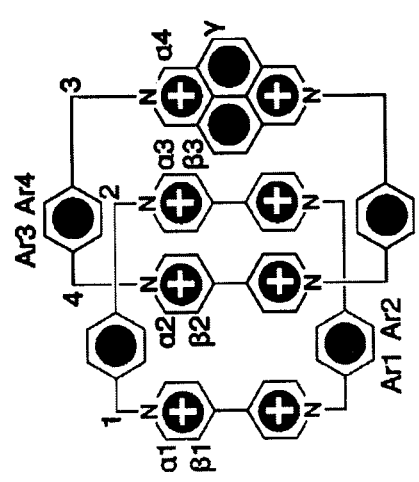
FIG. 6A shows a $^1H$ NMR Spectrum (500 MHz, $CD_3CN$, 298 K) of $AC.8PF_6$.
Figure 6A:
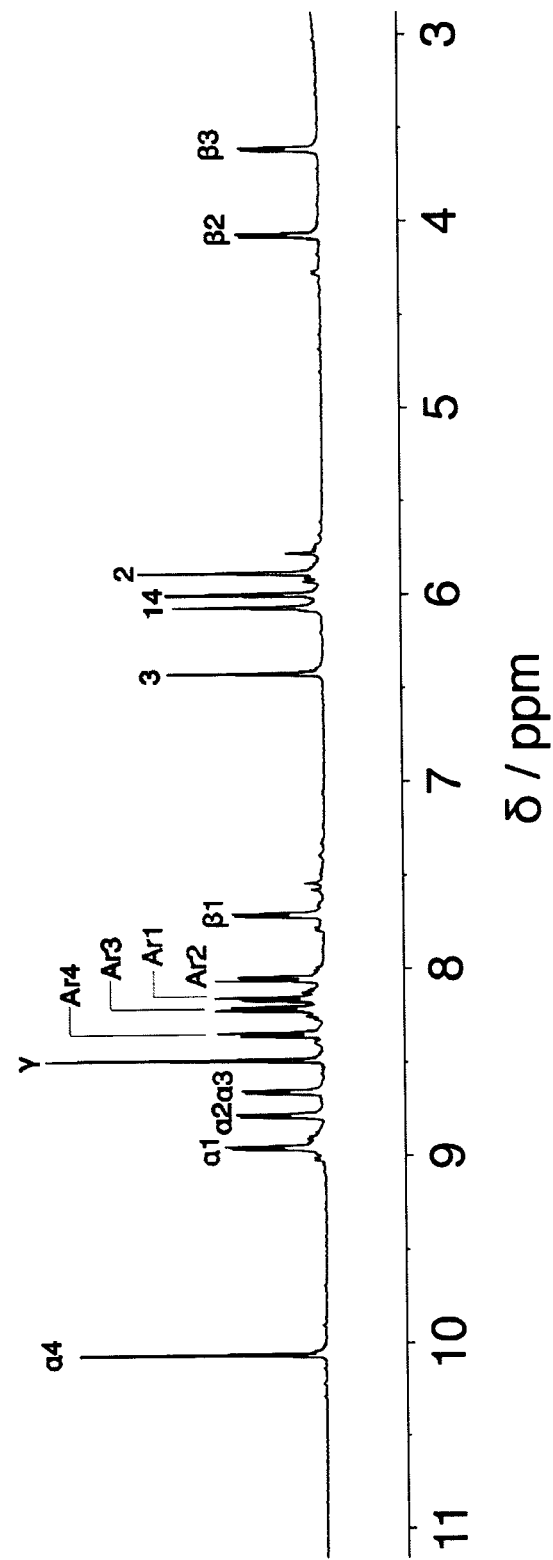

Since AC.7PF$_6$ is a paramagnetic compound, its oxidized form—namely, AC.8PF$_6$—was characterized by NMR spectroscopy. The $^1$H NMR spectrum (FIG. 6A) of AC.8PF$_6$ was recorded in CD$_3$CN at 298 K. It reveals that two proton resonances of β2 and β3 are very much shifted to high field on account of the 'shielding effect' enforced by the mechanical bond.

Figure 6B:
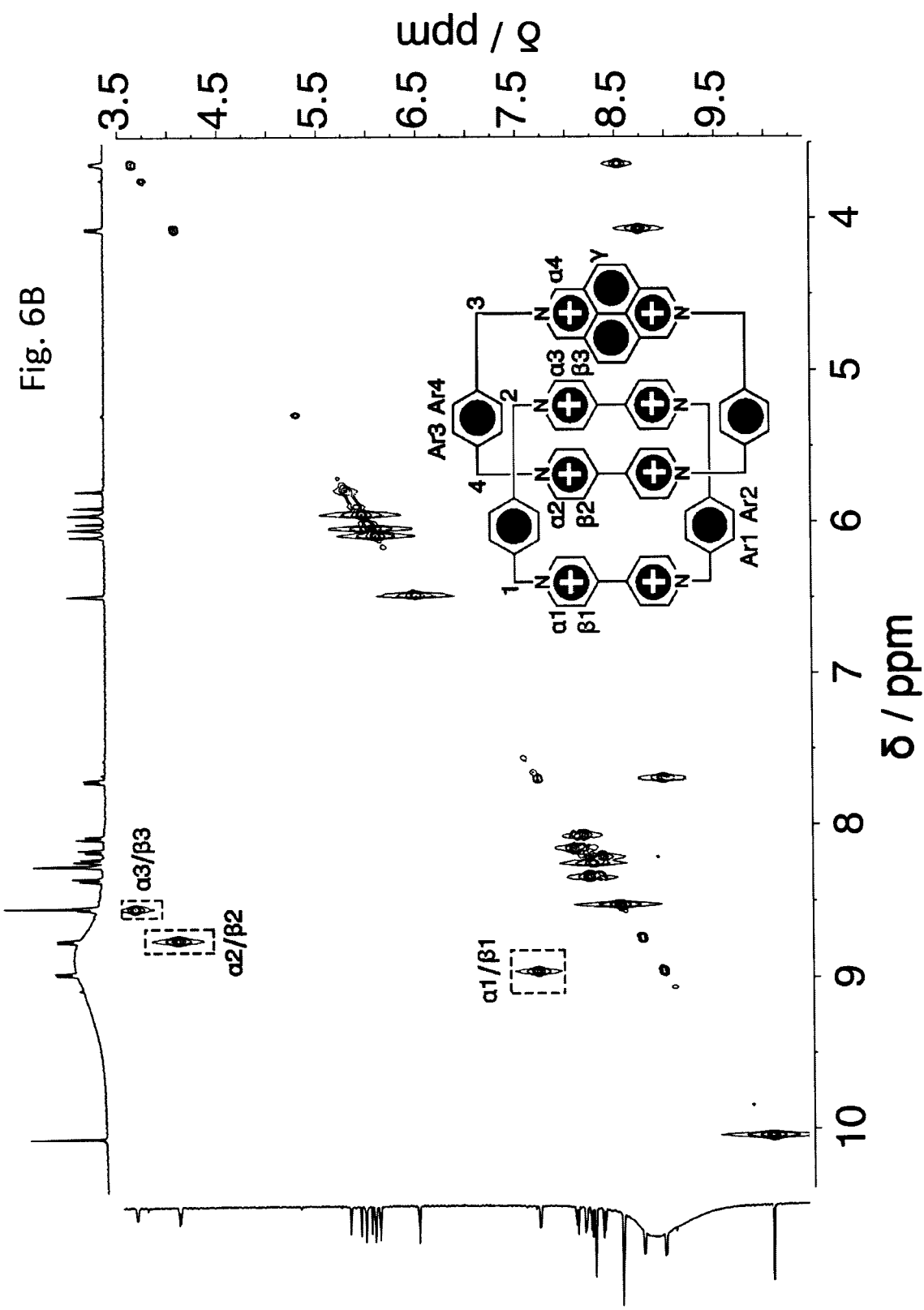
FIG. 6B shows a $^1H$-$^1H$ gCOSY NMR Spectrum (500 MHz, $CD_3CN$, 298 K) of $AC.8PF_6$.

The assignments of proton resonances have been made based on $^1$H-$^1$H gCOSY (FIG. 6B) obtained in CD$_3$CN at room temperature. The key correlation peaks are labeled in the 2D NMR spectrum.

$^1$H NMR Spectra of SC.8PF$_6$

Figure 8A:
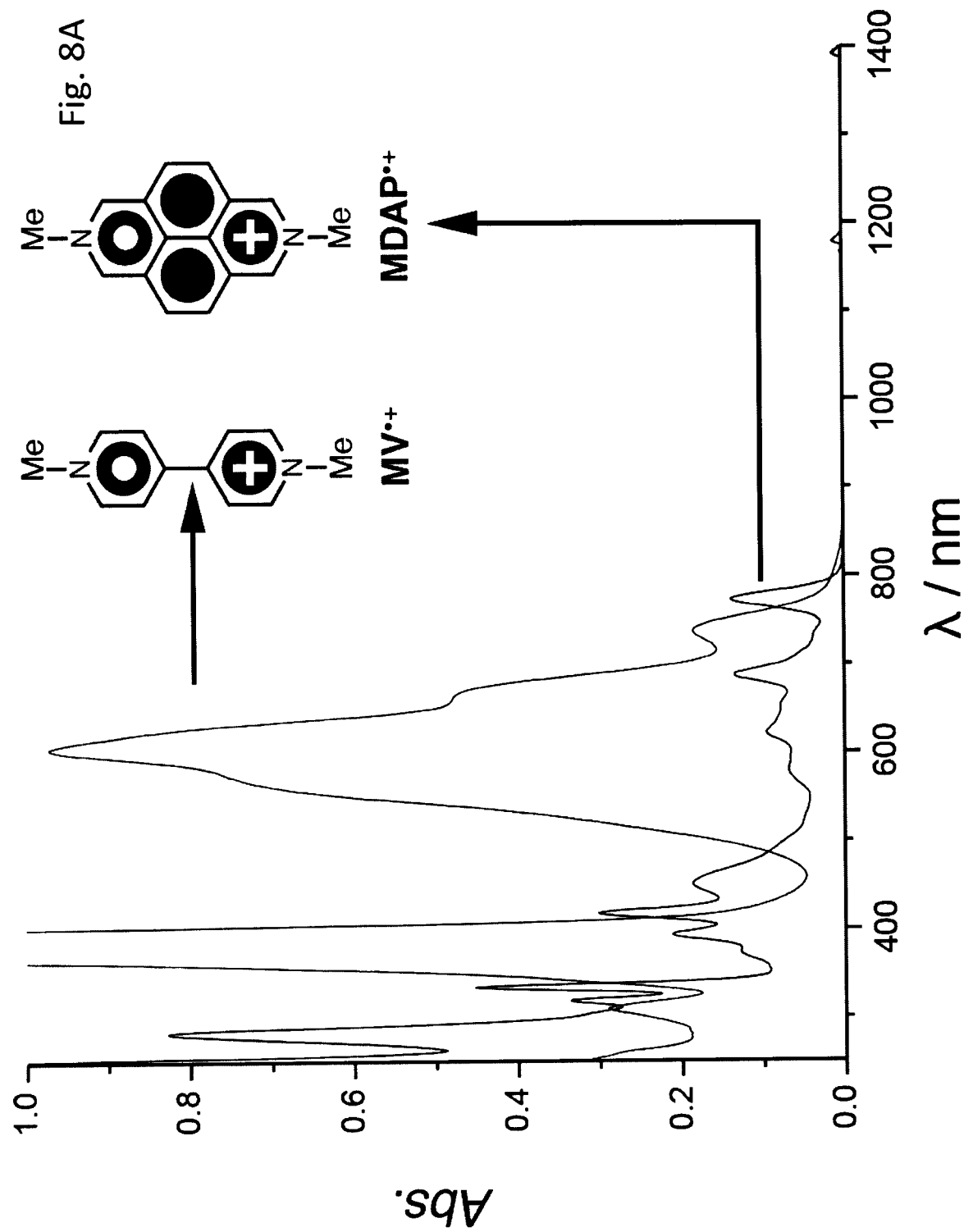
FIG. 8A shows UV-Vis-NIR Absorption Spectra (50 μM, MeCN, optical length: 1 cm) of $MV^{·+}$ and $MDAP^{·+}$.

SC.7PF$_6$ was oxidized with NO.PF$_6$ before being subjected to NMR spectroscopic analysis. In the $^1$H NMR spectrum (FIG. 7A) of SC.8PF$_6$, the upfield shift of the resonance for the β proton indicates the formation of the mechanically interlocked structure. In addition, compared with the resonance for the a proton in the two central BIPY$^{2+}$ units in AC$^{8+}$, those in SC$^{8+}$ are shifted to higher field because the additional 2,7-diazapyrenium unit in SC$^{8+}$ exerts a stronger 'shielding effect'. Again, the assignments have been made based on $^1$H-$^1$H gCOSY (FIG. 8A) obtained in CD$_3$CN at room temperature. The key correlation peaks are labeled in the spectrum.

UV-Vis-NIR Absorption of MV$^{\cdot+}$ and MDAP$^{\cdot+}$

The UV-Vis-NIR absorption spectra (FIG. 8A) of MV$^{\cdot+}$ and MDAP$^{\cdot+}$, which were obtained by reducing the corresponding MV$^{2+}$ and MDAP$^{2+}$ dications using Zn dust, reveal that both of them exhibit characteristic radical absorption bands centered around 600 nm, despite the fact that the molar absorption coefficient of MDAP$^{\cdot+}$ is much lower than that of MV$^{\cdot+}$.

UV-Vis-NIR Absorption of MDAP$^{\cdot+}$+CBPQT$^{2(\cdot+)}$, MV$^{\cdot+}$⊂CBPQT$^{2(\cdot+)}$ and MV$^{\cdot+}$⊂DAPQT$^{2(\cdot+)}$.

The UV-Vis-NIR absorption spectra (FIG. 8B) show that the methyl viologen MV$^{\cdot+}$ radical cation can form trisradical complexes with both CBPQT$^{2(\cdot+)}$ and DAPQT$^{2(\cdot+)}$ supported by the absorption bands centered on 920 and 1100 nm, respectively. The mixture of MDAP$^{\cdot+}$ and CBPQT$^{2(\cdot+)}$, however, fails to form the corresponding trisradical complex as indicated by the lack of the NIR absorption bands. This observation can be explained by the fact that the cavity of CBPQT$^{2(\cdot+)}$ is not large enough to accommodate MDAP$^{\cdot+}$.

Association Constant Determination

Figure 9A:
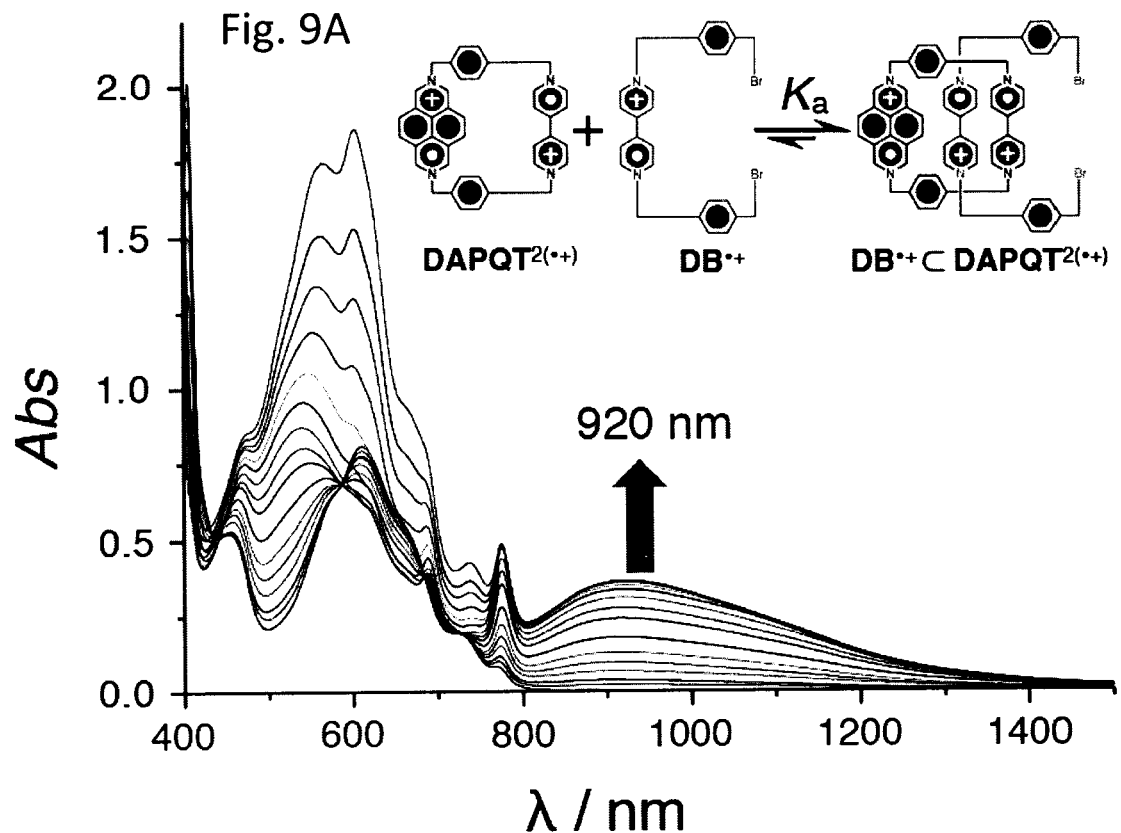
FIG. 9A shows stacked UV-Vis-NIR spectra obtained by titrating $DB^{·+}$ into a solution of $DAPQT^{2(·+)}$.
Figure 9B:
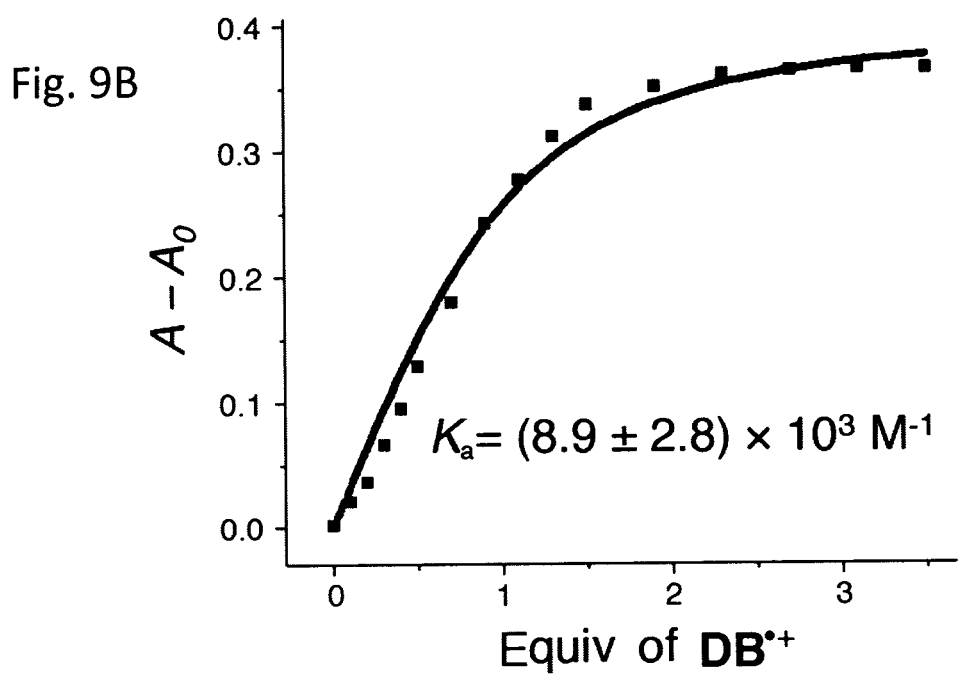
FIG. 9B shows a binding isotherm simulation.
Figure 10A:
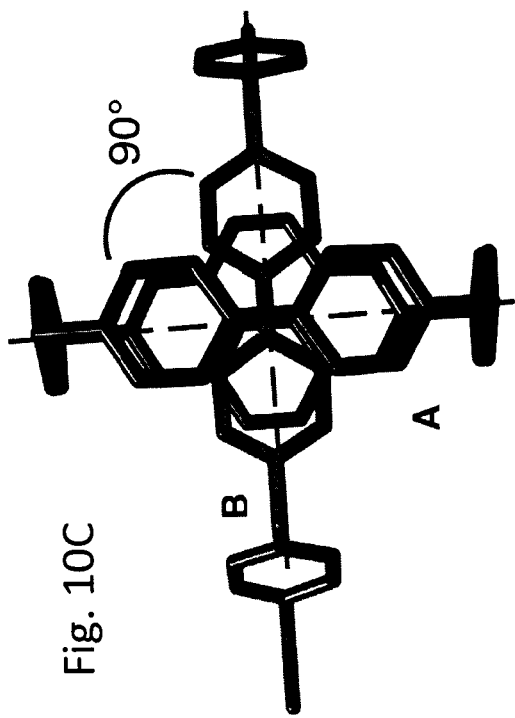
FIGS. 10A-10D show the solid-state superstructure of $(DB \subset DAPQT)^{2·4+}$.
Figure 10B:
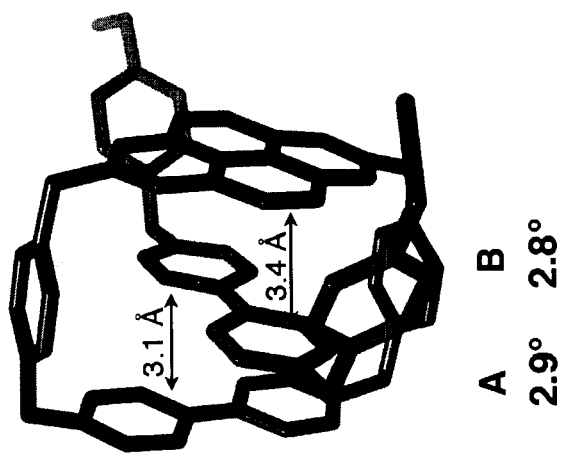
Figure 10C:
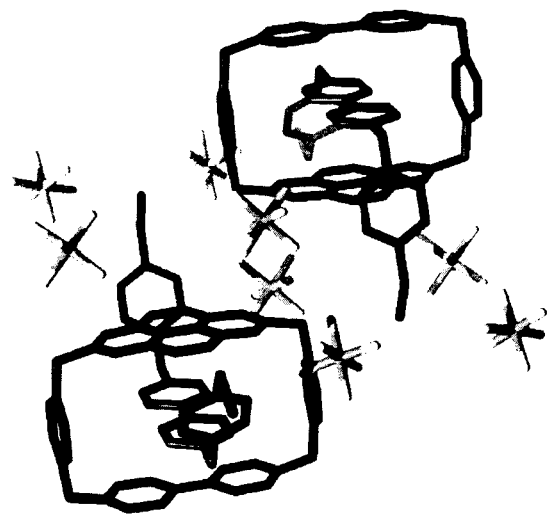
Figure 10D:
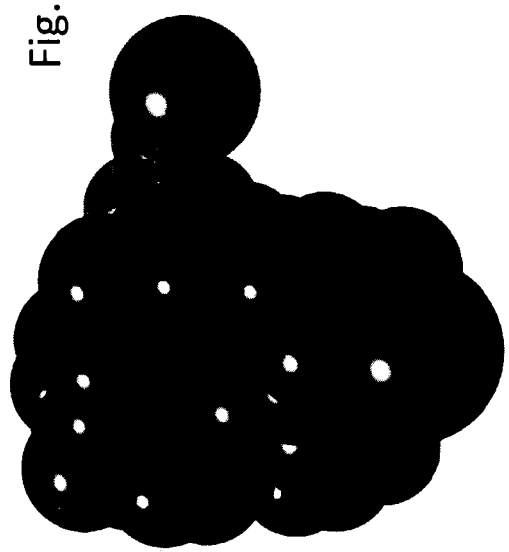
Figure 11A:
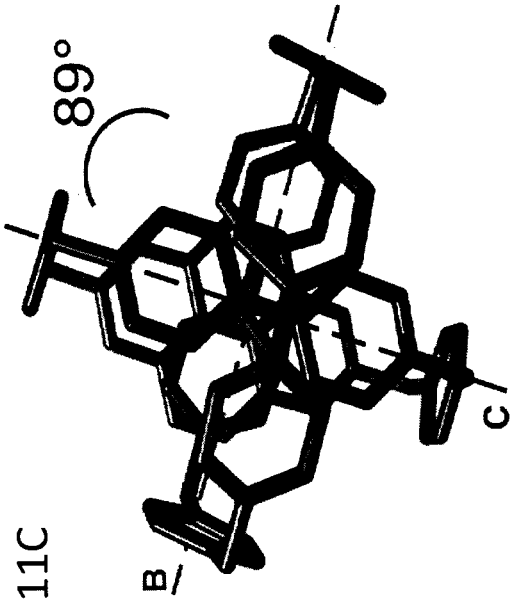
FIGS. 11A-11D show the solid-state structure of $AC^{·7+}$.
Figure 11C:
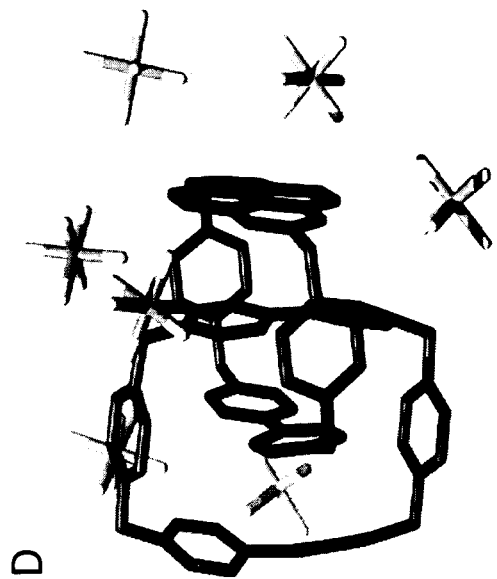
Figure 11B:
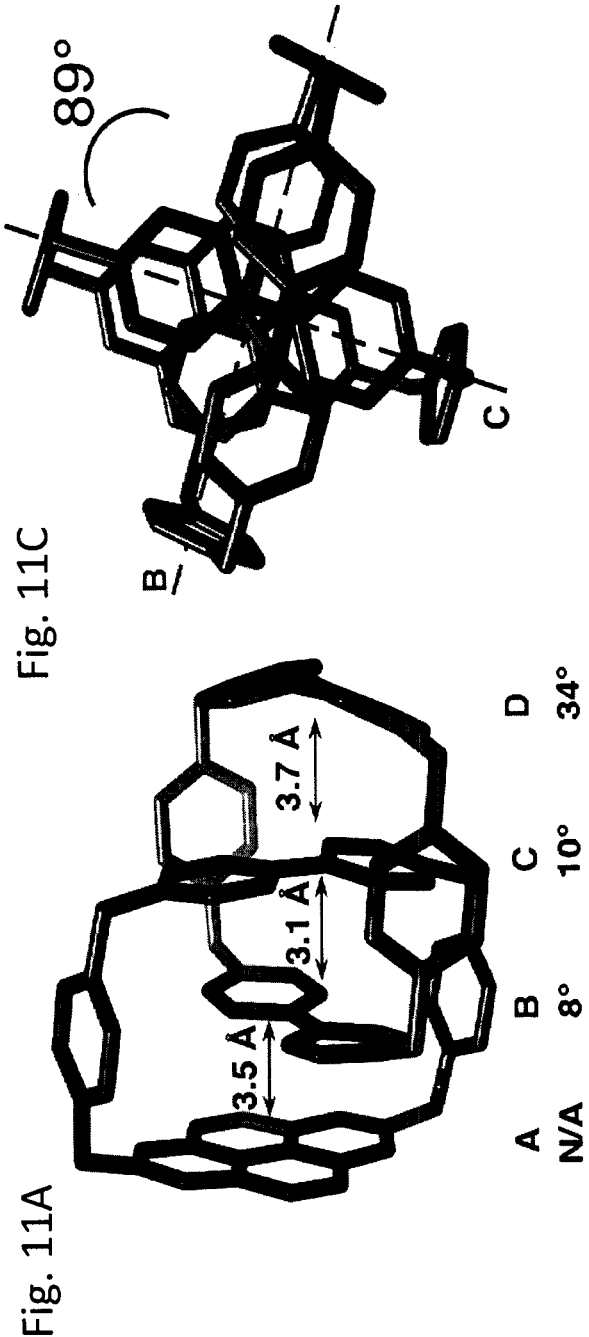
Figure 11D:
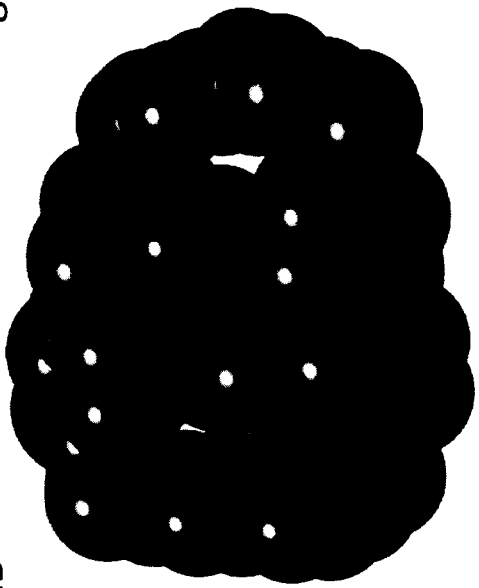
Figure 12C:
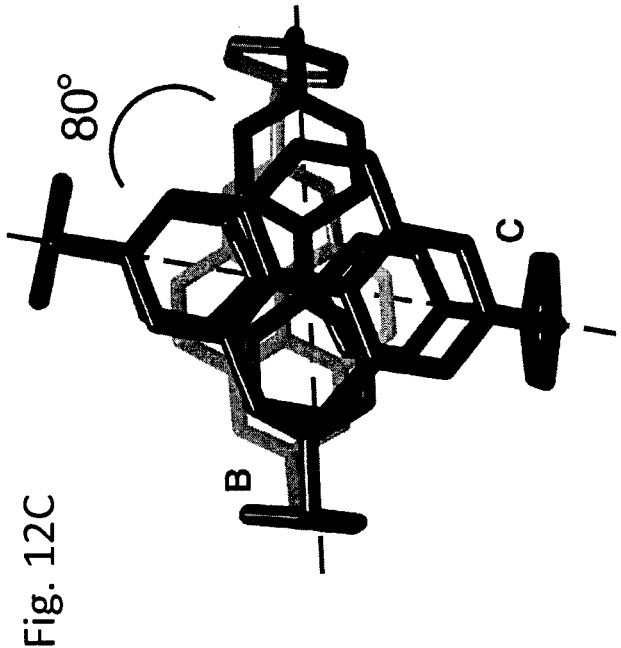
FIGS. 12A-12D show the solid-state structure of $SC^{·7+}$.
Figure 12D:
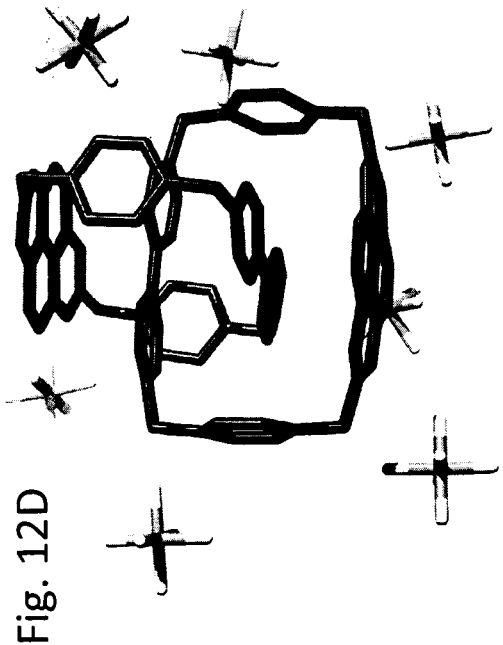
Figure 12A:
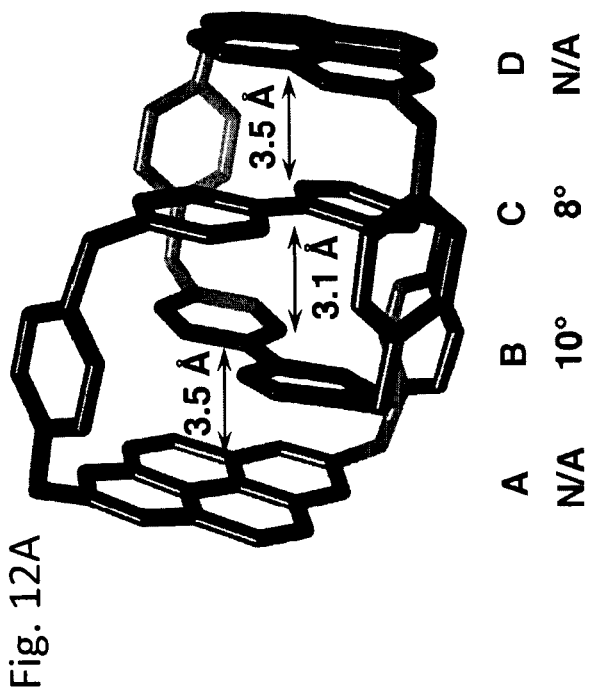
Figure 12B:
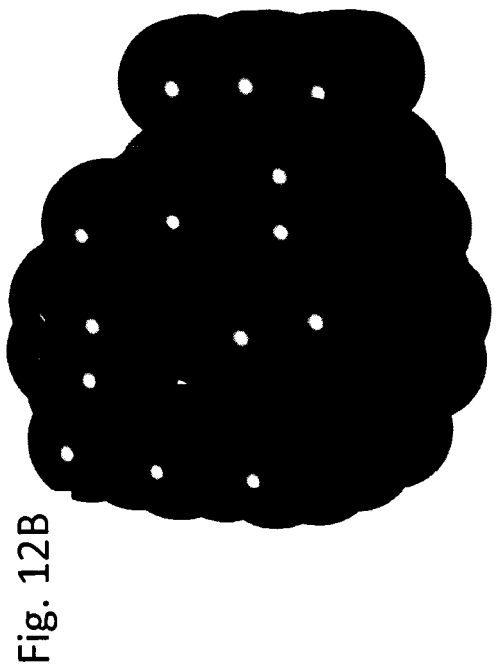

The measurement of the association constant (K$_a$) for the formation of the hetero trisradical complex between the DB$^{\cdot+}$ radical cation and the DAPQT$^{2(\cdot+)}$ bis(radical cation) in MeCN was carried out under Ar in a glovebox. An excess of Zn (20 mg) dust was added separately to solutions of DB$^{2+}$ (15 mM) and DAPQT$^{4+}$ (0.5 mM) in degassed MeCN (5 mL) contained in two separate vials. After both reaction mixtures had been stirred for 30 min and the reduction was complete, they were filtered into another two vials to give solutions (5 mL×2) of DB$^{\cdot+}$ (15 mM) and DAPQT$^{2(\cdot+)}$ (0.5 mM), respectively. The concentrated solution of DB$^{\cdot+}$ was added incrementally to the solution of DAPQT$^{2(\cdot+)}$. The UV-Vis spectra were recorded one after the other. The stacked spectra (FIG. 9A) show that, upon the addition of Dr, a new absorption band centered on 920 nm emerges and reaches a maximum when ca. 3 equiv of DB$^{\cdot+}$ has been added. From the UV-Vis-NIR titration experiment, a plot (FIG. 9A, black dot) of absorption intensity at 920 nm against the equiv of DB$^{\cdot+}$ was obtained and a non-linear least squares data treatment[Thordarson, P. *Chem. Soc. Rev.* 2011, 40, 1305-1323] (FIG. 9B, red line) gave an association constant of (8.9±2.8)×10$^3$ M$^{-1}$.

Electrochemistry

The electrochemistries of both SC.7PF$_6$ and AC.7PF$_6$ were investigated and compared with that of HC.7PF$_6$. Differential pulse voltammetry (DPV) reveals (FIGS. 5A-5C) that AC$^{\cdot7+}$ exhibits (FIG. 5C) six redox processes and seven discrete redox states, whereas SC$^{\cdot7+}$ has (FIG. 5A) only four redox processes and five redox states on account of its higher symmetry. In contrast, there are five redox processes and six redox states in the differential pulse voltammogram (FIG. 5B) of HC.7PF$_6$. The introduction of the DAP$^{2+}$ units to replace the BIPY$^{2+}$ units in this octacationic [2]catenane system modulates the stereoelectronic structures and hence achieves a consecutive series of five, six, and seven redox states in the resulting SC.7PF$_6$ (0, 4+, 6+, 7+, and 8+), HC.7PF$_6$ (0, 2+, 4+, 6+, 7+, and 8+), and AC.7PF$_6$ (0, 1+, 2+, 4+, 6+, 7+, and 8+), respectively, which make these catenanes ideal for applications as memory devices.

(DB⊂DAPQT).4PF$_6$ Crystalization a) Methods. Single crystals of (DB⊂DAPQT).4PF$_6$ were grown in a glovebox under Ar by preparing a 1 mL solution of 0.5 mM DAPQT.4PF$_6$ and 0.5 mM DB.2PF$_6$ in MeCN, followed by the addition of an excess of Zn dust. The resulting suspension was filtered and the filtrate divided between four culture tubes. Slow vapor diffusion of $^i$Pr$_2$O into the MeCN solutions led to the formation of purple crystals during a three-week period. A suitable crystal was selected and mounted in inert oil and transferred to the cold gas stream of a Bruker Kappa Apex2 diffractometer. The crystal was kept at 100 K during the data collection. Using Olex2 [Dolomanov et al. *J. Appl. Cryst.* 2009, 42, 339-341.], the structure was solved with the XT[Sheldrick, G. M. *Acta Cryst.* 2015, A71, 3-8.] structure solution program using direct methods and refined with the ShelXL[Sheldrick, G. M. *Acta Cryst.* 2008, A64, 112-122.] refinement package using least squares minimization. The solid-state superstructure of (DB⊂DAPQT)$^{2.4+}$ is shown in FIGS. 10A-10D.

b) Crystal data. Monoclinic, space group P2$_1$/m (no. 11), a=11.0874(5) Å, b=17.3630(7) Å, c=18.0711(8) Å, β=97.398(3°), V=3449.9(3) Å$^3$, Z=2, T=100.0 K, μ(Cu$_{K\alpha}$)=3.408 mm$^{-1}$, D$_{calc}$=1.689 g mm$^{-3}$, 6312 reflections measured (7.088°≤2θ≤133.578°), 6312 unique (R$_{sigma}$=0.0273) which were used in all calculations. The final R$_1$ was 0.0705 (I>2σ(I)) and wR$_2$ was 0.2137 (all data).

c) Refinement details. The crystal under investigation was found to be non-merohedrally twinned. The orientation matrices for the two components were identified using the program Cell Now (Sheldrick, 2005), and the data were processed using both orientation matrices with SAINT. The exact twin matrix identified by the integration program was found to be (0.515 0.001-0.488/0.003-1.000-0.001/-1.506-0.001-0.515). The second domain is rotated from first domain by 180° about the reciprocal lattice a-c axis. The absorption correction was carried out using TWINABS V2008/4 (Sheldrick, 2008) to create an HKLF 5 file, which was used in all refinements. The twin fraction refined to a value of 0.173(2).

AC.7PF$_6$ Crystalization a) Methods. Single crystals of AC.7PF$_6$ were grown on the bench-top by slow vapor diffusion of $^i$Pr$_2$O into a 1.0 mM solution in MeCN over the course of a week. A suitable crystal was selected and mounted in inert oil and transferred to the cold gas stream of a Bruker Kappa Apex2 diffractometer. The crystal was kept at 100 K during data collection. Using Olex2[Dolomanov et al. *J. Appl. Cryst.* 2009, 42, 339-341.], the structure was solved with the XM[Sheldrick, G. M. *Acta Cryst.* 2015, A71, 3-8.] structure solution program using dual space and refined with the XL[Sheldrick, G. M. *Acta Cryst.* 2008, A64, 112-122.] refinement package using least squares minimization. The solid-state structure of AC.7PF$_6$ is shown in FIGS. 11A-11D.

b) Crystal data. Triclinic, space group P$\bar{1}$ (no. 2), a=13.4859(7) Å, b=16.4625(8) Å, c=22.4987(11) Å, α=86.055(2)°, β=88.919(2)°, γ=82.503(2)°, V=4940.3(4) Å$^3$, Z=2, T=99.99 K, μ(Cu$_{K\alpha}$)=2.367 mm$^{-1}$, D$_{calc}$=1.580 g mm$^{-3}$, 17492 reflections measured (3.936°≤2θ≤136.69°), 17492 unique (R$_{int}$=0.0000, R$_{sigma}$=0.0321) which were used in all calculations. The final R$_1$ was 0.0809 (I>2σ(I)) and wR$_2$ was 0.2347.

c) Refinement details. The crystal used for this experiment was found to be nonmerohedrally twinned. Although the data were processed through TWINABS, the de-twinned HKLF 4 format file was found to provide a better refinement. Attempts to refine against both twin components gave a twin fraction of approximately 20%. The disordered PF$_6^-$ anion was refined with similar distance (SADI) and enhanced rigid bond (RIGU) restraints.

d) Solvent treatment details. The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell=199.7 Å$^3$ [4.0%] Total electron count/cell=41.9.

SC.7PF$_6$ Crystallization a) Methods. Single crystals of SC.7PF$_6$ were grown on the bench-top by slow vapor diffusion of $^i$Pr$_2$O into a 1.0 mM solution in MeCN over the course of a week. A suitable single crystal was selected and mounted in inert oil and transferred to the cold gas stream of a 'Bruker APEX-II CCD' diffractometer. The crystal was kept at 100 K during data collection. Using Olex2[Thordarson, P. *Chem. Soc. Rev.* 2011, 40, 1305-1323], the structure was solved with the XM[Dolomanov et al. *J. Appl. Cryst.* 2009, 42, 339-341.] structure solution program using dual space and refined with the XL[Sheldrick, G. M. *Acta Cryst.* 2015, A71, 3-8.] refinement package using least squares minimization. The solid-state structure of SC.7PF$_6$ is shown in FIGS. 12A-12D.

b) Crystal data. triclinic, space group P$\bar{1}$ (no. 2), a=13.3492(5) Å, b=27.9262(13) Å, c=31.5473(18) Å, α=73.377(4)°, β=89.810(4)°, γ=80.969(3)°, V=11118.6(9) Å$^3$, Z=4, T=100.03 K, μ(Cu$_{K\alpha}$)=2.040 mm$^{-1}$, D$_{calc}$=1.286 g mm$^{-3}$, 52846 reflections measured (9.382°≤2θ≤118.244°), 31303 unique (R$_{int}$=0.0671, R$_{sigma}$=0.0996) which were used in all calculations. The final R$_1$ was 0.1428 (I>2σ(I)) and wR$_2$ was 0.4038 (all data).

c) Refinement details. The disordered PF$_6^-$-counterions were refined with similar distance restraints (SADI) to keep the geometry reasonable. The enhanced rigid bond restraint (RIGU) was applied globally.

d) Solvent treatment details. The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell=3555.8 Å$^3$ [32.0%] Total electron count/cell=429.5

REFERENCES (1) Gomberg, M. *J. Am. Chem. Soc.* 1900, 22, 757.
(2) (a) Nishinaga, T.; Komatsu, K. *Org. Biomol. Chem.* 2005, 3, 561; (b) Zaitsev, V.; Rosokha, S. V.; Head-Gordon, M.; Kochi, J. K. *J. Org. Chem.* 2006, 71, 520; (c) *Stable Radicals: Fundamentals and Applied Aspects of Odd-Electron Compounds*; Hicks, R., Ed.; Wiley, 2011; (d) Wen, J.; Havlas, Z.; Michl, J. *J. Am. Chem. Soc.* 2015, 137, 165.
(3) Cafiso, D. S. *Acc. Chem. Res.* 2014, 47, 3102.
(4) (a) Morita, Y.; Nishida, S.; Murata, T.; Moriguchi, M.; Ueda, A.; Satoh, M.; Arifuku, K.; Sato, K.; Takui, T. *Nat. Mater.* 2011, 10, 947; (b) Aqil, A.; Vlad, A.; Piedboeuf, M.-L.; Aqil, M.; Job, N.; Melinte, S.; Detrembleur, C.; Jerome, C. *Chem. Commun.* 2015, 51, 9301.
(5) (a) Hünig, S.; Erk, P. *Adv. Mater.* 1991, 3, 225; (b) Hicks, R. G.; Lemaire, M. T.; Öhrström, L.; Richardson, J. F.; Thompson, L. K.; Xu, Z. *J. Am. Chem. Soc.* 2001, 123, 7154; (c) Tasoglu, S.; Yu, C. H.; Gungordu, H. I.; Guven, S.; Vural, T.; Demirci, U. *Nat. Commun.* 2014, 5, 4702; (d) Oliva, J.; Alcoba, D.; Oña, O.; Torre, A.; Lain, L.; Michl, J. *Theor. Chem. Acc.* 2015, 134, 1.
(6) Kosower, E. M.; Cotter, J. L. *J. Am. Chem. Soc.* 1964, 86, 5524.
(7) In solution, the (BIPY$^{.+}$)$_2$ radical cationic dimers can be stabilized in the presence of receptors. See example: Jeon, W. S.; Ziganshina, A. Y.; Lee, J. W.; Ko, Y. H.; Kang, J.-K.; Lee, C.; Kim, K. *Angew. Chem. Int. Ed.* 2003, 42, 4097.
(8) Fahrenbach, A. C.; Barnes, J. C.; Lanfranchi, D. A.; Li, H.; Coskun, A.; Gassensmith, J. J.; Liu, Z.; Benitez, D.; Trabolsi, A.; Goddard, W. A., III; Elhabiri, M.; Stoddart, J. F. *J. Am. Chem. Soc.* 2012, 134, 3061.
(9) Barnes, J. C.; Fahrenbach, A. C.; Cao, D.; Dyar, S. M.; Frasconi, M.; Giesener, M. A.; Benitez, D.; Tkatchouk, E.; Chernyashevskyy, O.; Shin, W. H.; Li, H.; Sampath, S.; Stern, C. L.; Sarjeant, A. A.; Hartlieb, K. J.; Liu, Z.; Carmieli, R.; Botros, Y. Y.; Choi, J. W.; Slawin, A. M. Z.; Ketterson, J. B.; Wasielewski, M. R.; Goddard, W. A., III; Stoddart, J. F. *Science* 2013, 339, 429.
(10) (a) Zhu, Z.; Fahrenbach, A. C.; Li, H.; Barnes, J. C.; Liu, Z.; Dyar, S. M.; Zhang, H.; Lei, J.; Carmieli, R.; Sarjeant, A. A.; Stern, C. L.; Wasielewski, M. R.; Stoddart, J. F. *J. Am. Chem. Soc.* 2012, 134, 11709. (b) Sun, J.; Wu, Y.; Wang, Y.; Liu, Z.; Cheng, C.; Hartlieb, K. J.; Wasielewski, M. R.; Stoddart, J. F. *J. Am. Chem. Soc.* 2015, 137, 13484.
(11) Ashton, P. R.; Boyd, S. E.; Brindle, A.; Langford, S. J.; Menzer, S.; Pérez-Garcia, L.; Preece, J. A.; Raymo, F. M.; Spencer, N.; Stoddart, J. F.; White, A. J. P.; Williams, D. J. *New J. Chem.* 1999, 23, 587.
(12) Lilienthal, N. D.; Enlow, M. A.; Othman, L.; Smith, E. A. F.; Smith, D. K. *J. Electroanal. Chem.* 1996, 414, 107.
(13) (14) DAP$^{2+}$ dications are known to be good π-acceptors. See example: Rama, T.; López-Vidal, E. M.; Garcia, M. D.; Peinador, C.; Quintela, J. M. *Chem. Eur. J.* 2015, 21, 9482.
(14) Chen, L.; Wang, H.; Zhang, D. W.; Zhou, Y.; Li, Z. T. *Angew. Chem. Int. Ed.* 2015, 54, 4028.

(15) Cheng, C.; McGonigal, P. R.; Liu, W.-G.; Li, H.; Vermeulen, N. A.; Ke, C.; Frasconi, M.; Stern, C. L.; Goddard, W. A., III; Stoddart, J. F. *J. Am. Chem. Soc.* 2014, 136, 14702.

(16) Barnes, J. C.; Frasconi, M.; Young, R. M.; Khdary, N. H.; Liu, W.-G.; Dyar, S. M.; McGonigal, P. R.; Gibbs-Hall, I. C.; Diercks, C. S.; Sarjeant, A. A.; Stern, C. L.; Goddard, W. A., Ill; Wasielewski, M. R.; Stoddart, J. F. *J. Am. Chem. Soc.* 2014, 136, 10569.

(17) Zhao, Y.; Truhlar, D. *Theor. Chem. Acc.* 2008, 120, 215.

We claim:

1. A salt comprising a mechanically interlocked molecule characterized by a monoradical heptacationic oxidation state and seven counteranions per mechanically interlocked molecule,
   wherein the mechanically interlocked molecule comprises a first ring mechanically interlocked with a second ring,
   wherein the first ring comprises (i) a 4,4'-bipyridinium subunit or a derivative thereof and (ii) a diazapyrenium subunit or a derivative thereof;
   wherein the second ring comprises (i) a 4,4'-bipyridinium subunit or a derivative thereof and (ii) a diazapyrenium subunit or a derivative thereof or a 4,4'-bipyridinium subunit or a derivative thereof; and
   wherein the mechanically interlocked molecule is an air-stable radical characterized by seven nitrogen in a cationic state and one nitrogen having an unpaired electron.

2. The salt of claim 1, wherein the first ring comprises a compound of Formula III,

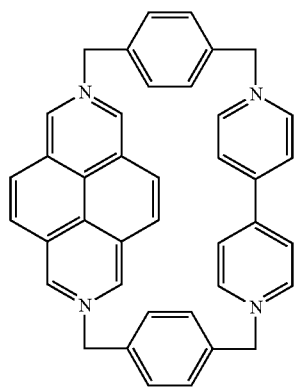

(Formula III)

or a derivative thereof,
   wherein the first ring is characterized as a tetracation and each nitrogen is in the cationic state or the first ring is characterized as a monoradical triscation and three nitrogen are in the cationic state and one nitrogen has the unpaired electron.

3. The salt of claim 1, wherein the second ring comprises (i) a compound of Formula III,

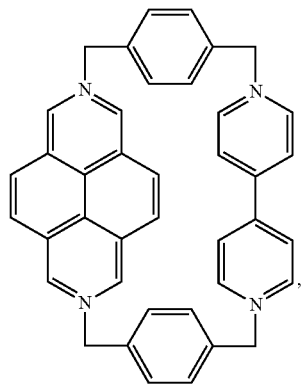

(Formula III)

or a derivative thereof or (ii) a compound of Formula IV,

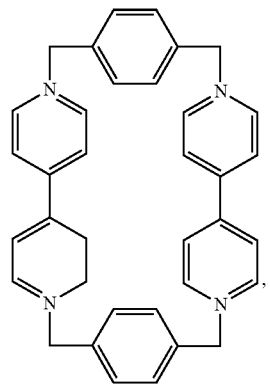

(Formula IV)

or a derivative thereof,
   wherein the second ring is characterized as a tetracation and each nitrogen is in the cationic state or the second ring is characterized as a monoradical triscation and three nitrogen are in the cationic state and one nitrogen has the unpaired electron.

4. The salt of claim 1, wherein the mechanically interlocked molecule comprises a composition of Formula V,

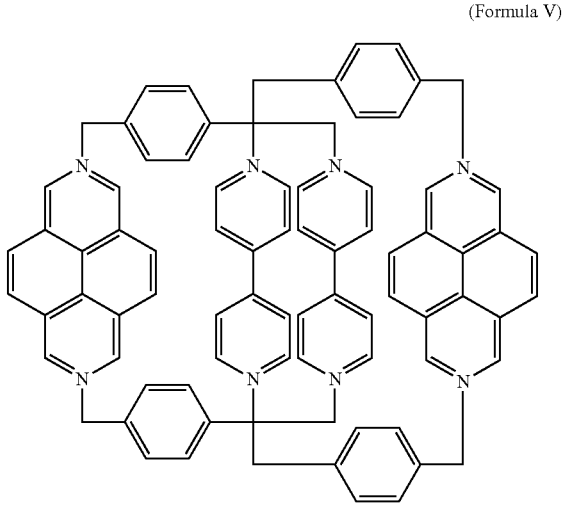

(Formula V)

or a derivative thereof.

5. The salt of claim 1, wherein the mechanically interlocked molecule comprises a composition of formula VI,

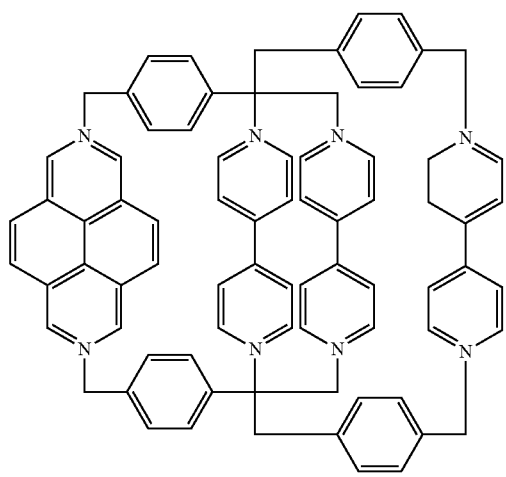

(Formula VI)

or a derivative thereof.

6. The salt of claim 1, wherein the counteranion is $PF_6^-$.

7. The salt of claim 1, wherein the salt is prepared by (a) providing a radical cationic inclusion complex and reacting the complex with (i) 2,7-diazapyrene, (ii) 4,4'-bipyridine, or a derivative of either (i) or (ii).

8. A crystalline composition comprising the salt of claim 1 having a molecular packing arrangement defined by triclinic space group $P\bar{1}$ (no. 2).

9. The crystalline composition of claim 8, wherein the composition has lattice parameters of a=13.5±0.1 Å, b=16.5±0.1 Å, c=22.5±0.1 Å, α=86.1±0.1°, β=88.9±0.1°, γ=82.5±0.1°.

10. The crystalline composition of claim 8, wherein the composition has lattice parameters of a=13.3±0.1 Å, b=27.9±0.1 Å, c=31.5±0.1 Å, α=73.4±0.1°, β=89.8±0.1°, γ=81.0±0.1°.

11. A memory device comprising the salt of claim 1.

* * * * *